United States Patent [19]

Allington et al.

[11] Patent Number: 5,158,675
[45] Date of Patent: * Oct. 27, 1992

[54] GRADIENT SYSTEM

[75] Inventors: Robert W. Allington; Daniel G. Jameson, both of Lincoln, Nebr.

[73] Assignee: Isco, Inc., Lincoln, Nebr.

[*] Notice: The portion of the term of this patent subsequent to Sep. 26, 2006 has been disclaimed.

[21] Appl. No.: 535,565

[22] Filed: Jun. 11, 1990

Related U.S. Application Data

[60] Division of Ser. No. 355,881, May 19, 1989, Pat. No. 4,981,597, which is a continuation of Ser. No. 23,913, Mar. 9, 1987, abandoned, which is a continuation-in-part of Ser. No. 838,332, Mar. 10, 1985, abandoned.

[51] Int. Cl.$^5$ .............................................. B01D 15/08
[52] U.S. Cl. ................................. 210/198.2; 210/101; 210/143; 137/88; 417/503
[58] Field of Search .................... 137/88, 93, 240, 266, 137/605; 417/18, 22, 503; 210/101, 120, 136, 143, 149, 188, 198.2, 656; 73/61.1 C; 422/70; 436/161

[56] References Cited

U.S. PATENT DOCUMENTS

| | | | |
|---|---|---|---|
| 707,567 | 8/1902 | Edson | 210/120 |
| 2,729,338 | 1/1956 | Heigl | 210/341 |
| 3,701,609 | 10/1972 | Bailey | 210/198.2 |
| 3,771,542 | 11/1973 | Williams | 137/93 |
| 3,985,019 | 10/1976 | Boehme | 210/198.2 |
| 3,985,021 | 10/1976 | Achener | 210/198.2 |
| 4,054,522 | 10/1977 | Pinkerton | 210/188 |
| 4,116,046 | 9/1978 | Stein | 210/198.2 |
| 4,128,476 | 12/1978 | Rock | 210/101 |
| 4,136,708 | 1/1979 | Cosentino | 417/503 |
| 4,137,011 | 1/1979 | Rock | 417/22 |
| 4,233,156 | 11/1980 | Tsukada | 210/198.2 |
| 4,310,420 | 1/1982 | Honishi | 210/198.2 |
| 4,311,586 | 11/1982 | Baldwin | 210/101 |
| 4,388,184 | 6/1983 | Brous | 210/101 |
| 4,422,942 | 12/1983 | Allington | 210/101 |
| 4,437,812 | 3/1984 | Abu-Shumays | 210/198.2 |
| 4,448,692 | 5/1984 | Nakamoto | 210/198.2 |
| 4,595,495 | 6/1986 | Yotam | 210/101 |
| 4,600,365 | 7/1986 | Riggenmann | 417/246 |
| 4,733,152 | 3/1988 | Allington | 210/198.2 |
| 4,869,374 | 9/1989 | Allington | 210/198.2 |
| 4,986,919 | 1/1991 | Allington | 210/198.2 |

OTHER PUBLICATIONS

"Monitoring Solenoid Valve Position" by Lewis Research Center, Instrumentation Technologies, vol. 17, No. 6, Jun. 1970, p. 67.

Keatos, Spectroflow 430, Publication #251-42221 (1984) pp. 1 and 2.

Primary Examiner—Ernest G. Therkorn
Attorney, Agent, or Firm—Vincent L. Carney

[57] ABSTRACT

To supply a programmed gradient to a high pressure pump for introduction into a column, a mixer, degasser and accumulator communicates with the high pressure pump to supply fluid thereto, having a volume no more than 150 times the chamber volume of the high pressure pump. The mixer, degasser and accumulator includes temperature sensors which sense when the mixer, degasser and accumulator has been emptied to a level where it cannot respond to a demand for fluid from said high pressure pump and provides a signal to a low pressure pump which responds by cycling to again fill the mixer, degasser and accumulator. Upon receiving a demand signal, the low pressure pump fills by drawing fluid from a plurality of fluid sources to compose the gradient being used at that time, with the pump slowing during valve opening and closing so as to avoid cavitation.

14 Claims, 9 Drawing Sheets

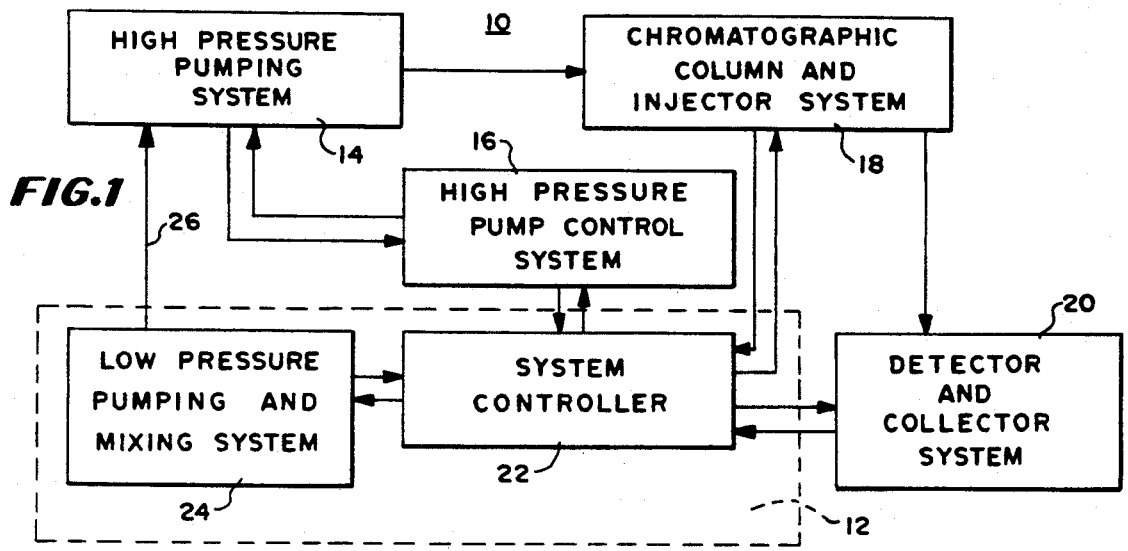

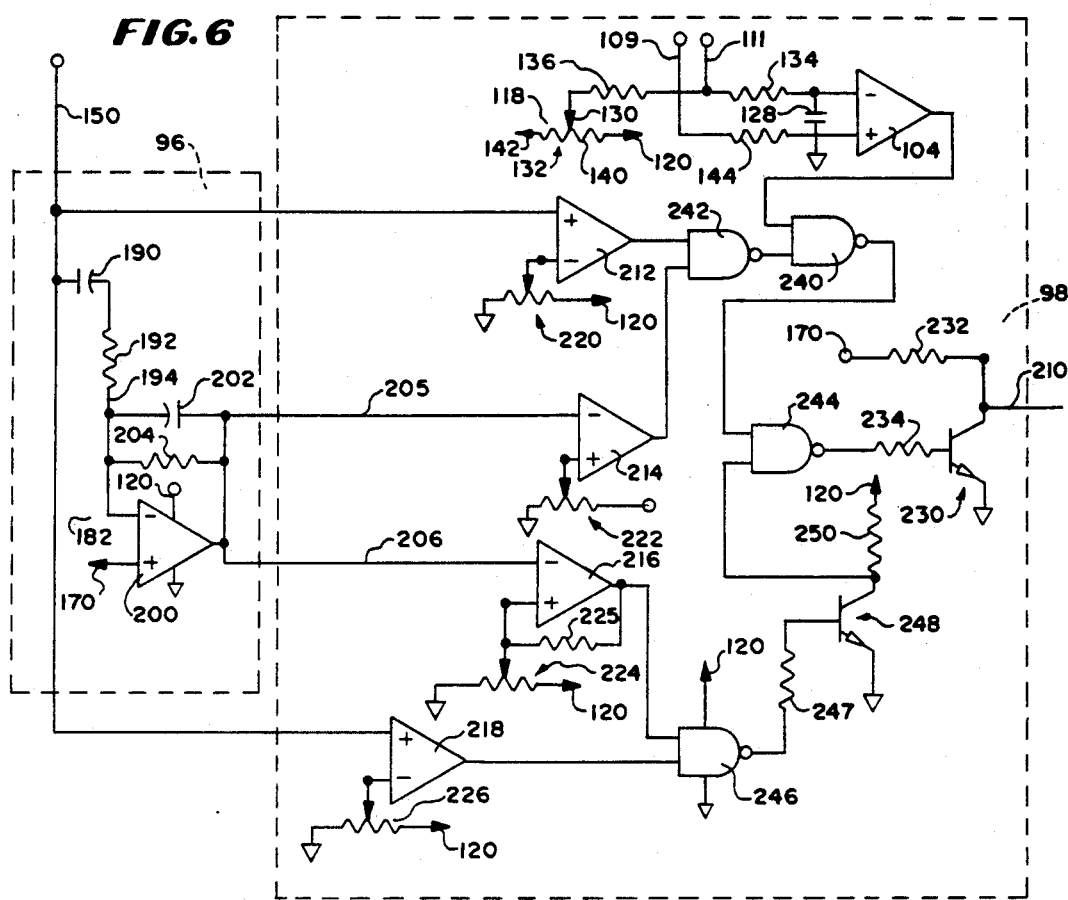
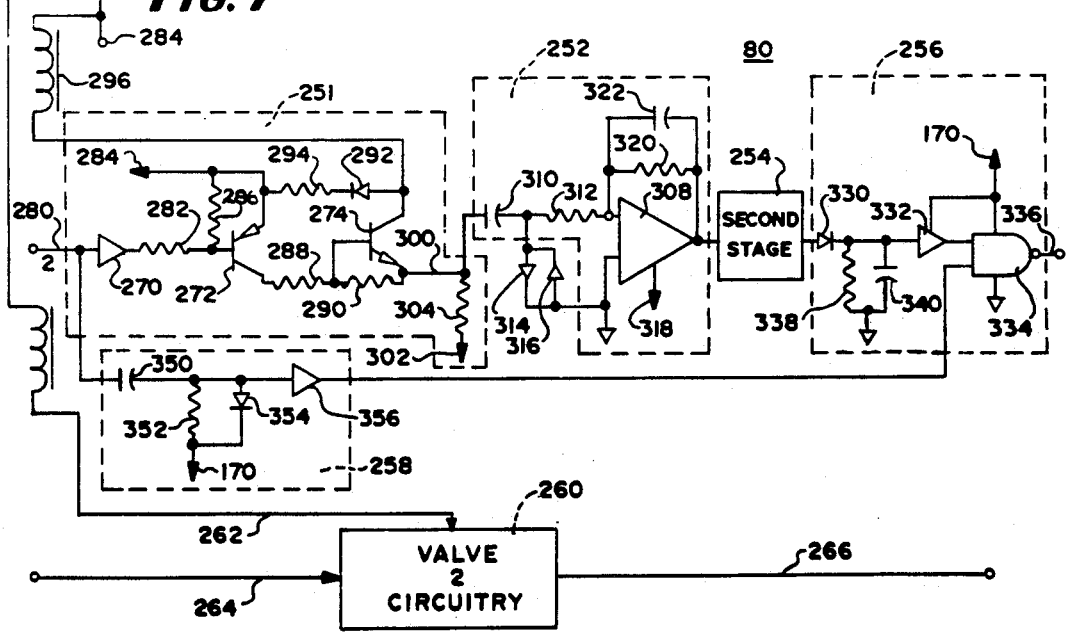

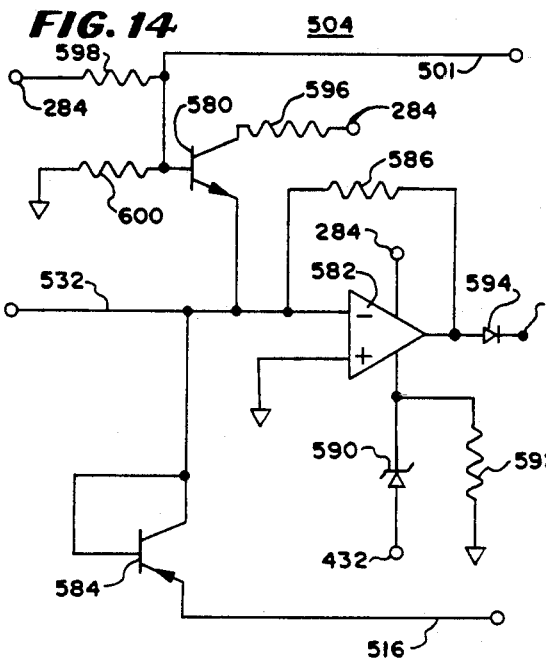
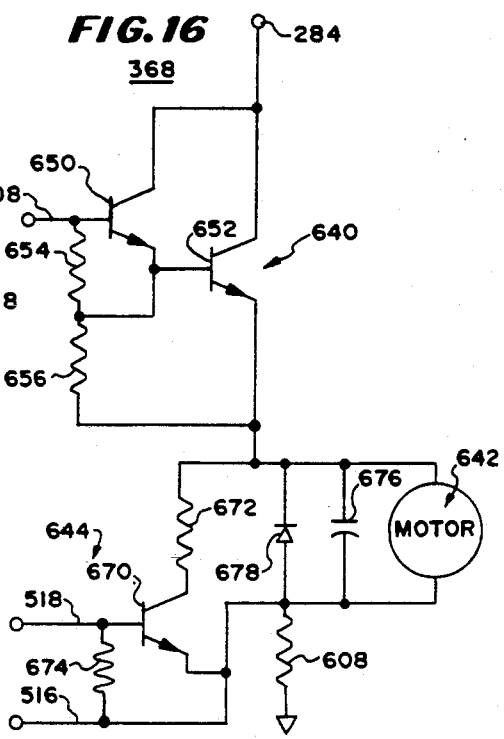
FIG. 14
FIG. 15
FIG. 16

GRADIENT SYSTEM

RELATED CASES

This application is a division of U.S. application Ser. No. 07,/355,881, filed May 19, 1989, now U.S. Pat. No. 4,981,597 which is a file wrapper continuation of U.S. application Ser. No. 07/023,913, filed Mar. 9, 1987, now abandoned which is a file wrapper continuation-in-part of U.S. application Ser. No. 06/838,332, filed Mar. 10, 1985 now abandoned, and are assigned to the same assignee as this application.

BACKGROUND OF THE INVENTION

This invention relates to gradient systems for liquid chromatography.

Gradient programmers are known which control the flow of two or more solvents to a mixer to provide a constant flow rate of influent to a chromatographic column from the mixer while varying the proportions of the two or more solvents.

In one prior art programmer of this type, two pumps pump different solvents into a mixer, which mixes them into a final influent to the chromatographic column. The rate of pumping of the two pumps is varied with time so that their sum is constant but the proportions of the solvent supplied by each differ.

This type of prior art gradient former has several disadvantages such as: (1) when one of the pumps is pumping at a very low rate or when both are pumping at nearly the same but differing rates, substantial inaccuracies occur caused by pulsations; and (2) in a high pressure liquid chromatograph, the two high pressure pumps increase the cost of the system.

In another prior art system, three low pressure pumps directly feed one high pressure pump. Such a system is disclosed in U.S. Pat. No. 4,311,586. This system has a disadvantage of being expensive.

In still another prior art system, digitally controlled valves are controlled in response to a computer command and each supplies a solvent to a chromatographic pump from a different reservoir. A system of this type is disclosed in U.S. Pat. No. 4,128,476 issued Feb. 2, 1982, to John V. Rock. This system has a disadvantage of risking overlapping valve openings and thus imprecise compositions of liquids.

SUMMARY OF THE INVENTION

Accordingly, it is an object of the invention to provide an improved chromatographic system.

It is a further object of the invention to provide a novel gradient former.

It is a still further object of the invention to provide a novel gradient elution system which provides a good mixing efficiency both at high constant flow rates and low constant flow rates of influent into a chromatographic column.

It is a still further object of the invention to provide a novel gradient elution system for liquid chromatography in which the proportioning of solvents from one or more sources is independent of changes in valve response and viscosity of liquids.

It is a still further object of the invention to provide a novel high pressure gradient elution system in which the programming of the mixture of solvents forming the influent to the chromatographic column is independent of the action of the high pressure pump.

It is a still further object of the invention to provide a high pressure chromatographic system which includes a mixer that receives fluid from a low pressure system in sufficient quantities to maintain a reservoir and supplies the fluid on demand to a high pressure pump.

It is a still further object of the invention to provide a gradient former in which a mixer reservoir draws mixed solvents at a low pressure in proportions controlled by the gradient programmer when the liquid level within it falls below a predetermined level and supplies the mixture upon demand to its outlet.

It is a still further object of the invention to provide a novel degasser for a liquid chromatograph.

It is a still further object of the invention to provide a gradient former in which a pump draws fluid in a return stroke from one or more sources in controlled proportions and supplies them to a mixer in a forward stroke.

It is a still further object of this invention to provide a gradient former in which a mixer demands liquid when it drops below a certain level and a pump responds by drawing fluid from one or more sources to insert into the mixer with the speed of the pump being controlled to avoid cavitation taking into account valve opening time.

It is a still further object of the invention to provide a novel combination mixer, degasser and reservoir for solvents.

It is a still further object of the invention to provide a novel valve control system that monitors the time duration between energization of a valve and its opening and corrects the time for initiating energization for changes in this time duration.

It is a still further object of the invention to provide a novel gradient former usable with high pressure pumps of different capacity and design.

It is a still further object of this invention to provide a novel valve system for supplying liquids from a plurality of sources of fluids for use in a liquid chromatograph.

In accordance with the above and further objects of the invention, a low pressure pump draws fluid from one or more sources of solvent and supplies the fluid at low pressure to a mixer, with the mixer signaling when it is able to receive more fluid. A high pressure pump removes fluid from the mixer to supply it to the liquid chromatograph.

Advantageously, the low pressure pump has multiple speeds and the sources of solvents are connected through valves to the pump. During its filling stroke, the pump adjusts its speed to prevent cavitation of liquid flowing into the low pressure pump, taking into account valve opening time. The speed of the pump during delivery is sufficiently fast to cause mixing when expelled into the mixer. To provide better control of the composition of liquids, the signals caused by a change in inductance in solenoid coils is detected (1) when valves are energized; and (2) when opened. Changes in the difference between the time of energization and opening of the valves is stored. The timing of the pump and valve switching are corrected accordingly on the next cycle. The valves open to supply solvent from one source only for each time period the pump slows to prevent two sources from supplying solvent at one time. A tree arrangement of valves minimizes the number of valves for multiple solvents and improves precision in composition.

As a feature of this system, the low pressure pump and mixer, during start up of the high pressure pump, can supply a selected fluid or selected fluids to the high pressure pump under some pressure in sufficient quantities to prime the high pressure pump. For this purpose, the control system that fills the mixer on demand is bypassed and the pump continues to pump fluid to the mixer from which it flows to the pump under pressure of a spring biased check valve which is leaky to air under normal conditions but creates pressure under continuous pumping to prime the high pressure pump. The inlet check valve for air entering the mixer is not spring biased.

As can be understood from the above description, the chromatographic system of this invention has several advantages such as: (1) the mixing efficiency of this system is independent of the flow rate of the high pressure pump that is supplied with solvents; (2) it is able to prime an associated high pressure pump; (3) it is able to mix several solvents with precision even though some of the solvents may be at a low amount; (4) it is an economical approach to high pressure gradient liquid chromatography; (5) it can operate in a stand-by condition automatically at low speeds with one solvent; (6) it provides efficient degassing; (7) changes in the time between energization of a valve and its opening is taken into account in switching; and (8) a tree valving system improves the precision of mixing to a programmed composition.

SUMMARY OF THE DRAWINGS

The above-noted and other features of the invention will be better understood from the following detailed description when considered with reference to the accompanying drawings in which:

FIG. 1 is a block diagram of a liquid chromatographic system incorporating the gradient system of this invention;

FIG. 2 is a block diagram of a gradient system which forms a portion of the block diagram of FIG. 1;

FIG. 6 is a schematic circuit diagram of another portion of the embodiment of FIG. 4;

FIG. 7 is a schematic circuit diagram of a portion of the embodiment of FIG. 3;

FIG. 14 is a schematic circuit diagram of still another portion of the block diagram of FIG. 12;

FIG. 15 is a schematic circuit diagram of still another portion of the block diagram of FIG. 12;

FIG. 16 is a schematic circuit diagram of still another portion of the block diagram of FIG. 8;

DETAILED DESCRIPTION

Figure 3:
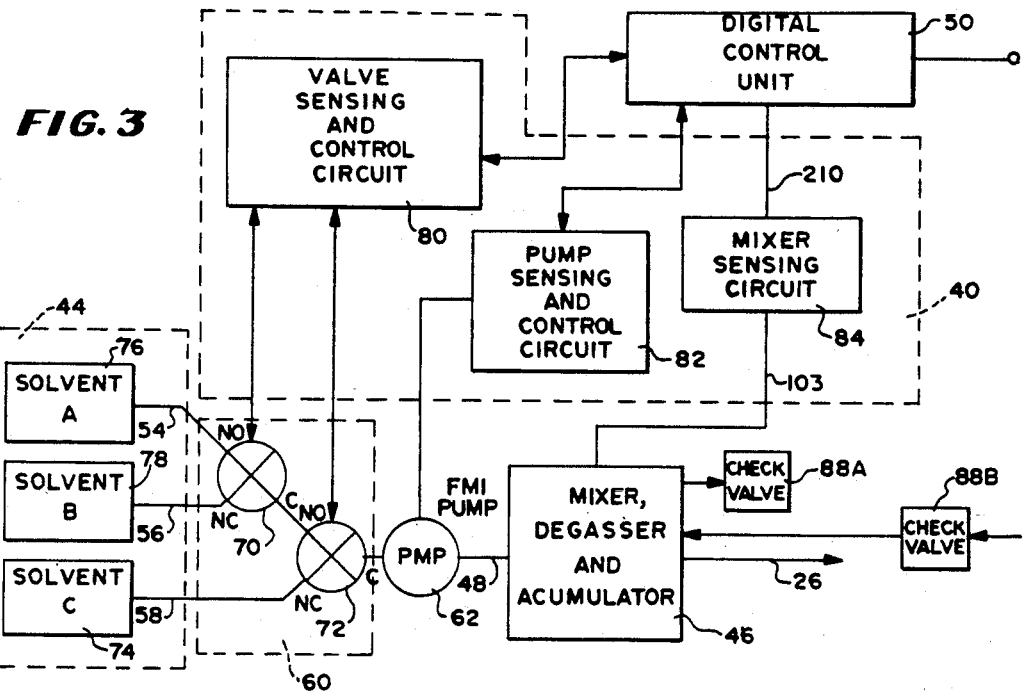
FIG. 3 is a block diagram of a portion of the gradient system of FIG. 1.

In FIG. 1, there is shown a block diagram of chromatographic system 10 having a gradient system 12, a high pressure pumping system 14, a high pressure pump control system 16, a chromatographic column and injector system 18 and a detector and collector system 20. The gradient system 12 communicates with the high pressure pumping system 14 to supply solvents thereto mixed in proportions in accordance with a gradient program. The high pressure pumping system 14 communicates with the chromatographic column and injector system 18 to supply the influent thereto for detection and at times collection by the detector and collector system 20.

The gradient system 12 is electrically connected to the high pressure pump control system 16, the chromatographic column and injector system 18 and the detector and collector system 20 to receive signals therefrom for data management and to apply signals thereto for controlling other units.

The high pressure pumping system 14, the high pressure pump control system 16, the chromatographic column and injector system 18 and the detector and collector system 20 are not part of this invention except insofar as they cooperate with the gradient system 12 to enable high pressure gradients to be delivered to a liquid chromatographic column with precision at both low flow rates and high flow rates.

The gradient system 12 includes a low pressure pumping and mixing system 24 and a general system controller 22. The general system controller 22 contains the the gradient program as well as other control circuits such as, for example, for injecting samples into the chromatographic column or providing data acquisition and processing functions in conjunction with the detector and collector system 20. The general system controller 22 is not part of the invention except insofar as it provides signals to the low pressure pumping and mixing system 24 which represent the gradient to be pumped.

The low pressure pumping and mixing system 24 mixes together solvents in proportions under the control of the system controller 22 and supplies them to the high pressure pumping system 14 at the rate required by the high pressure pumping system 14, supplying an efficiently mixed gradient independently of the flow rate demanded by the high pressure pumping system 14.

In FIG. 2, there is shown a block diagram of the gradient system 12 having a system controller 22, a low pressure pumping and mixing system 24 and a power supply 30. The power supply 30 and system controller 22 are not part of the invention except insofar as they cooperate with the low pressure pumping and mixing system 24 but the power supply 30 supplies power to other units and the system controller 22 provides certain data management and control functions.

In the preferred embodiment, the system controller 22 includes a microprocessor with a user input/output keyboard and display 52 electrically connected to a digital control unit 50 into which the user may insert information such as flow rate starting time and stopping time through the use of a conventional user input/output keyboard.

To provide solvents through conduit 26 to the high pressure pumping system 14 (FIG. 1), the low pressure pumping and mixing system 24 includes a plurality of solvent sources shown generally at 44, a pump, valve and motor assembly 42, an analog control circuit 40 and a mixer, degasser and accumulator 46. The solvent sources 44 are conventional solvents for liquid chromatography each contained in its own container which communicates by conduits with the pump, valve and motor assembly 42.

The analog control circuit 40 is connected to the digital control unit 50 to receive signals controlling starting time, time duration and gradient mixtures to be used in a chromatographic run. The analog control circuit 40 is electrically connected to the pump, valve and motor assembly 42 to control the mixing and the pumping of solvents to the mixer, degasser and accumulator 46. The mixer, degasser and accumulator 46 supplies signals to the analog control circuit 40 indicating when it is nearly empty and the analog control circuit 40 responds by causing the pump, valve and motor assembly 42 to supply a preprogrammed mixture of solvents to the mixer, degasser and accumulator 46 from the solvent sources 44.

In FIG. 3, there is shown the analog control circuit 40 electrically connected to the pump 62, the mixer, degasser and accumulator 46, a valve assembly 60, the solvent sources 44 and the digital control unit 50 to: (1) receive signals from the digital control unit 50, the pump 62, the valve assembly 60 and the mixer, degasser and accumulator 46; and (2) in accordance with such received signals control the valves within the valve assembly 60 and the pump 62.

To permit selection of solvents to be mixed in the pump 62, the valve assembly 60 includes a tree arrangement of valves communicating with the solvent sources 44 and the pump 62. The use of a tree in which only one of several paths can be open at a time to a plurality of solvent sources 44 simplifies switching functions since, when one path is open to select a solvent, all others are inherently closed without the need for the valves through which a solvent was previously flowing being deactivated. This renders the release time of the valve through which fluid is flowing less critical when a different fluid is to be selected. In the preferred embodiment, the valves are released when no fluid is being delivered by the pump 62 to the mixer, degasser and accumulator 46. The solvent is programmed to be removed from the supply vessels for 100 percent of the aspirating time of the pump.

In the preferred embodiment, the valve assembly 44 includes two three port valves, which are a first electrically activated valve 70 and a second electrically activated valve 72. The solvent sources 44 includes three solvent sources 74, 76 and 78. The valve 72 has its normally closed outlet port communicating with the pump 62, a first normally open inlet port communicating with a normally closed port of the valve 70 and a normally closed inlet port communicating with a source of solvent 74. A normally open inlet port of the valve 70 communicates with a source of solvent 76 and a normally closed inlet port of the valve 70 communicates with a source of solvent 78.

With this arrangement, the second valve 72 is normally in communication with the source of solvent 76 but may be switched to put it in communication with the source of solvent 78 by changing the valve 70. Moreover, both of those sources may be disconnected and the valve 72 may communicate instead with the source 74. Any of those sources may be selected or all of them in sequence to communicate with the pump 62 for pumping through a conduit 48 to the mixer, degasser and accumulator 46.

The mixer, degasser and accumulator 46 is sized so that it includes a volume of liquid at least sufficiently large to fill the cylinder of a high pressure pump so that the mixer, degasser and accumulator 46 is able to continuously supply fluid to the high pressure pump irrespective of the flow rate being pumped by the high pressure pump. The low pressure pump 62 is sized to be able to maintain the mixer, degasser and accumulator full and thus must either operate rapidly or have a sufficient size cylinder to be able to fill the mixer, degasser and accumulator 46 regardless of the rate of withdrawal by the high pressure pump. Its pump stroke must such that it permits adequate time for the valves 70 and 72 to open to apply solvent to the pump for mixing therein and pumping to the mixer, degasser and accumulator 46.

To enable the valves 70 and 72 to be more precisely controlled, the pump 62 and the mixer, degasser and accumulator 46, the analog control circuit 40 includes a valve sensing and control circuit 80, a pump sensing and control circuit 82 and a mixer sensing circuit 84. The valve sensing and control circuit 80 is electrically connected to the valves 70 and 72 to receive signals indicating whether they are energized on opening or moving from one position to another opening and supply controlling signals to open or close them.

The valve tree includes valves having relatively small, precision, valve ports so as to create a precise gradient. Large ports cause unpredictable changes in flow rates from different solvents when switching occurs between two solvents and may create a pressure drop of significance because of their size. To avoid cavitation and uncertainty in the liquid flowing into the pump, the pump speed is controlled thus reducing the rate of flow of the liquid at times to avoid unpredictable changes and cavitation. The pump is slowed to a low rate while the valves are opening, then gradually increased to a medium rate when the valves through which liquid is flowing are fully open and then slowed gradually for the next valve switching.

When the mixture is in the pump and a delivery stroke has started, the pump speed is increased to a level that aids in mixing when expelled into the mixer, with an average flow rate equaling the rate of the high-pressure pump average flow rate. To cause mixing, at least 50 percent of the volume expelled into the mixer in a pump cycle is expelled in no more than 9 percent of the time period of the cycle.

For this purpose, there are at least three pumping rates, a low rate for valve switching to change intake liquids, a medium rate for open valve solvent intake and a high rate for final delivery. In the preferred embodiment, the ratios of switching intake pumping rate to open valve intake pump motor speed pumping rate varies with position of plunger (half sinusoidal stroke speed at constant motor speed) are in the ranges of 1 to 1.5 and 1 to 5 and the range of open valve intake to final delivery pump motor speed rate ratios are in the ranges of 1 to 1.5 and 1 to 10. The actual flow rates will vary depending on the portion of the stroke but the maximum possible flow rates with such speeds will have the same ratios as the pump motor speeds described above. Although motor speeds are directly controlled, the end result is to avoid uncertainties and lack of precision in the inflow rates by requiring a low flow rate when the valves are switching, without completely stopping the motor and without making such abrupt changes in rate of flow as to cause cavitation.

The open valve or intermediate rate of flow is set to provide adequate flow rate without cavitation into the low pressure pump during refill to support its designed pumping rate, taking into consideration the low rates necessary to avoid cavitation during valve switching. The average of the pumping rate or high rate must be high enough to supply the needs of the high-pressure pump and must at times be high enough to cause mixing in the reservoir. The pump rate during valve switching is low enough to avoid cavitation and unpredictable flow from two solvents but otherwise as high as possible to provide as much contribution to inflow as possible and the intermediate flow rate is set to avoid cavitation with the highest precision valves possible.

When the high-pressure pump is operating at flow rates below a predetermined rate, which in one embodiment is 5 milliliters, the low-pressure pump cycle is started when the mixer signals empty and when the high-pressure pump is pumping at a rate above the predetermined rate, the low-pressure pump completes a fill cycle before the empty signal and starts a pump or delivery cycle on receiving an empty signal.

The pump sensing and control circuit 82 similarly is electrically connected to the pump 62 to sense the position of the pump and to change its speed when appropriate. The mixer sensing circuit 84 is electrically connected to: (1) the mixer, degasser and accumulator 46; and (2) the digital control unit 50. It senses when the mixer, degasser and accumulator 46 is empty and starts the pump through a cycle by sending signals to the control unit 50 which transmits signals to the pump sensing and control circuit 82 and to the valve sensing and control circuit 80 to cause the valves to open and supply solvent to the pump 62, which in turn pumps solvents into the mixer, degasser and accumulator, supply fluid to the high pressure pump irrespective of the flow rate being pumped by the high pressure pump. The pump 62 is sized to be able to maintain the mixer, degasser and accumulator full and thus must either operate rapidly or have a sufficient size cylinder to be able to fill the mixer, degasser and accumulator 46 regardless of the rate of withdrawal by the high pressure pump. Its pump stroke must be such that it permits adequate time for the valves 70 and 72 to open to apply solvent to the pump for mixing therein and pumping to the mixer, degasser and accumulator 46.

The mixer, degasser and accumulator 46 includes an overflow conduit connected to it through check valves 88. During priming of the high pressure pump, solvent is applied to the mixer, degasser and accumulator 46 in sufficient quantities to perform the priming without the requiring of an empty signal from the sensors therein. Under this circumstance, solvent may overflow through the check valve 88A and air may flow into the mixer, degasser and accumulator through check valve 88B.

The overflow valve 88A is spring biased liquid-tight, but not necessarily air tight, and closed to at least one-half pound per square inch to cause pressure to build in the mixer, degasser and accumulator but the valve 88B which permits air to enter the mixer, degasser and accumulator is not spring biased. Moreover, the valve 88A may be air leaky, but in any event air is permitted to freely enter and leave the mixer. The pressure in the mixer, degasser and accumulator is increased during a priming operation of the high pressure pump by causing a solvent to continuously flow into the mixer, degasser and accumulator while the high pressure pump is operating until the high pressure pump is primed. The fill signal is inhibited and the flow continues until the operator terminates the prime signal after the high-pressure pump has been primed.

Figure 4:
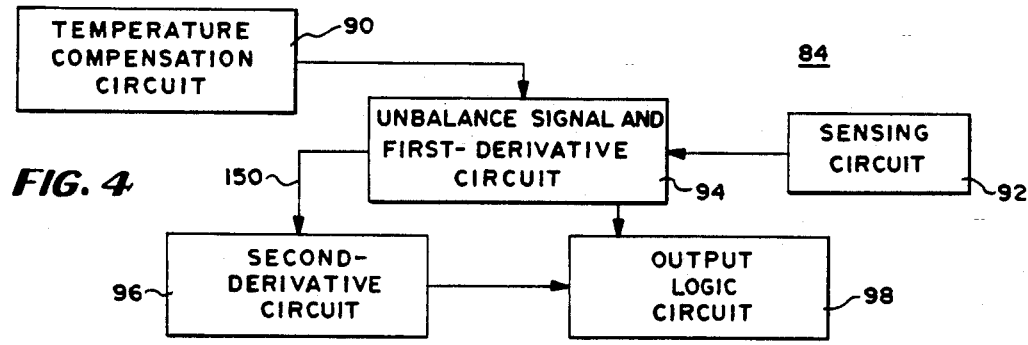
FIG. 4 is a block diagram of a portion of the system of FIG. 3.

In FIG. 4, there is shown a block diagram of the mixer sensing circuit 84 having a temperature compensation circuit 90, a sensing circuit 92, an unbalance signal and first-derivative circuit 94, a second-derivative circuit 96, and an output logic circuit 98.

The sensing circuit 92 is electrically connected to the unbalance signal and first-derivative circuit 94 to transmit a signal thereto when the mixer, degasser and accumulator 46 (FIGS. 2 and 3) is empty. The unbalance signal and first-derivative circuit 94, the output logic circuit 98; the second-derivative circuit 96 and the temperature compensation circuit 90 are connected together to permit transmittal of a temperature-compensated signal to the output logic circuit 98 and initiates a pumping and valve command to obtain more solvent in the mixer.

Figure 5:
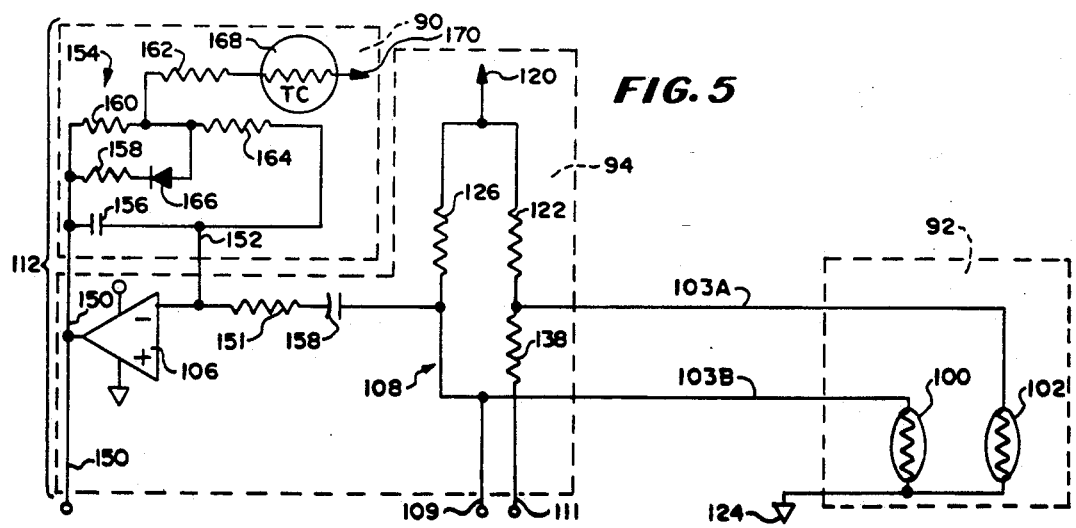
FIG. 5 is a schematic circuit diagram of a portion of the block diagram of FIG. 4.

In FIG. 5, there is shown a schematic circuit diagram of the sensing circuit 92, the unbalance signal and first-derivative circuit 94 and the temperature compensation circuit 90. The sensing circuit 92 senses an empty mixer and applies a signal to the unbalance signal and first-derivative circuit 94 which transmits the unbalance signal to the output logic circuit 98 (FIG. 4) and transmits its derivative, corrected through a connection with the temperature compensation circuit 90 to the second-derivative circuit 96 (FIG. 4).

To sense when the mixer, degasser and accumulator 46 (FIG. 3) is empty, the first and second thermistors 100 and 102 are mounted within it with the thermistor 102 being mounted at a location where it remains below the surface of the liquid in the mixer, degasser and accumulator 46 at all times and the thermistor 100 being mounted at a location where when the liquid falls below it, it is no longer cooled by the liquid and it warms, thus changing its resistance.

The capacity of the high pressure pump in the high pressure pumping system 14 and the mixer, degasser and accumulator 46 are selected so that there always remains within the mixer, degasser and accumulator 46 a level of liquid at the end of each stroke of the high pressure pump that covers the thermistor 102 to maintain a temperature equal to that of the temperature of the solvents in the mixer, degasser and accumulator 46. The thermistor 100 is mounted at the level below which the mixer, degasser and accumulator 46 is to be considered empty when the influent drops below it. The volume of container and the mixer, degasser and accumulator 46 above that level is equal at least to a full stroke of the low pressure pump 62.

With this arrangement, the temperature of the thermistor 102 serves as a reference. When the temperature of the thermistor 100 changes, it indicates that the solvent has dropped below it permitting it to be affected by the temperature of the air instead of that of the liquid. The thermistors 100 and 102 are both self-heated thermistors which maintain a temperature above that of the higher of the influent and ambient air in the preferred embodiment. The level thermistor should be self-heated so that it heats up in air more than the reference thermistor. By heating both of them, local temperature gradients in the solvent can be accommodated.

To obtain a signal which may indicate that the mixer, degasser and accumulator 46 is empty, the unbalance signal and first- derivative circuit 94 includes an output amplifier 106, a bridge circuit 108, and a differentiator circuit 112. The bridge circuit 108 is electrically connected to the thermistors 100 and 102, and to the differentiator circuit 112 and generates a signal when the resistance of the thermistory 100 changes. The differentiator circuit provides instantaneous information and the voltage level provides status information.

To compensate for temperature changes, the temperature compensation circuit 90 is electrically connected to the differentiating circuit 112 and to the output amplifier circuit 106 to correct for temperature changes in the bridge 108. With this circuit arrangement, changes in the resistance between the thermistors 100 and 102 cause an unbalance signal to be applied to the output conductors 109 and 111 indicating an empty condition in the mixer, degasser and accumulator 46 (FIG. 3). The unbalance signal is differentiated by the differentiator 112 and the derivative is amplified and applied to the second derivative circuit 96 (FIG. 4) through conductor 150 to provide a more sensitive indication of an empty condition for earlier detection.

When the ambient temperature changes, thermistor 168 reduces its resistance which increases the power of the differentiator by decreasing the feedback for amplifier 106 through resistors 160 and 164. This compensation is needed because thermistor 100 decreases in resistance on lead 103B and thus, the change in resistance decreases.

To provide a signal to the comparator output logic circuit 98 (FIG. 4) and differentiator 112 indicating that the liquid has dropped below the level-measuring thermistor 100, the bridge 108 includes a source 120 of a positive 12 volts electrically connected through two paths in parallel, which are: (1) the 432 ohm resistor 122 and the reference thermistor 102 to electrical common 124; and (2) the 432 ohm resistor 126 through level-measuring thermistor 100 to electrical common 124.

To differentiate the unbalance signal from the bridge 108, the differentiator 112 includes the temperature compensation circuit 90 and the amplifier circuit 106 in the unbalance signal and first derivative circuit 94 with a 15 K (kilohm) resistor 150 and a 3 uf (microfarad) capacitor 153 electrically connected in series between resistor 126 and the inverting input of the amplifier 106. The output of the operational amplifier 106 is electrically connected to: (1) the second-derivative circuit 96 through conductor 150 and (2) the temperature compensation circuit 90.

To provide temperature compensation, the temperature compensation circuit 90 includes a first conductor 150 electrically connected to the output of the output amplifier 106 and the second input conductor 152 connected to the inverting input of the amplifier 106 to form a feedback path around the amplifier 106. The compensation circuit includes a capacitor 156, four resistors 158, 160, 162 and 164, a diode 166, a thermistor 168 and a source of a positive five volts 170. The thermistor 168 is mounted to the panel and has a negative co-efficient of resistance whereas the thermistors 100 and 102 are mounted within the mixer and have negative coefficients of resistance.

One end of the thermistor 168 is connected to the source 170 of a positive five volts and the other end is connected: (1) to conductor 150 through the 732 ohm resistor 162 and the 48.7 K (kilohm) resistor 160 in series in the order named; (2) to conductor 150 through an alternate path including the resistor 162, the forward resistance of a 1N273 diode 166 and the 14.7 K resistor 158; (3) to conductor 150 through still another path including resistor 162, a 48.7 K resistor 164 and the 0.03 uf (microfarad) capacitor 156; and (4) to conductor 152 through resistors 162 and 164.

With this circuit arrangement, the thermistor varies the gain of the feedback network composed of resistors 160, 162 and 164 and varies the gain of the differentiator 112 to compensate for changes in ambient temperature and to provide a more reliable indication of the difference between the temperatures of the level thermistor 100 when the mixer, degasser and accumulator 46 (FIG. 2) is full and the temperatures of the level thermistor 100 in ambient air. The diode 166 and resistor 158 decrease the feedback gain corresponding to wet and dry conditions so that the wet to dry and dry to wet conditions so that the wet to dry and dry to wet transition signals are the same.

In FIG. 6, there is shown a schematic circuit diagram of the second derivative circuit 96 and the output logic circuit 98. The output logic circuit 98 receives signals on conductors 109 and 111 indicating an unbalance signal and signals on conductor 150, 205 and 206 from the second derivative circuit 96 from which it detects when the liquid level is sufficiently low to initiate a refill cycle of the low pressure pump by a sign on conductor 210 to the pump sensing and control circuit 82 (FIG. 3). The second derivative circuit 96 is electrically connected to conductor 150 to provide a second derivative for application to the output logic circuit 98 to improve the response time.

To form the second derivative of the first derivative signal applied to it by the first derivative circuit 94 on conductor 150, the differentiator circuit 96 includes a one microfarad capacitor 190 and a 4.7 K resistor 192 and amplifier 200. One place of the capacitor 190 is electrically connected to conductor 150 and its other plate is connected to one end of the resistor 192. The other end of the resistor 192 is electrically connected to the summing node 182 through conductor 194 at the inverting input of amplifier 200.

The second differentiator circuit includes an operational amplifier 200 a one uf feedback capacitor 202, a 200 K resistor 204 and the source 120 of positive 12 volts and the source 170 of positive 5 volts. The output of the operational amplifier 200 is electrically connected to the logic circuit through conductor 206 to provide a second derivative signal to the logic circuit.

Amplifier 200 has its non-inverting terminal electrically connected to the source 170 of a positive 5 volts and its rails connected between common and a positive 12 volt source 120. The capacitor and resistor feedback cause the amplifier to produce the second derivative and apply it to the logic circuit, thus indicating a rate of acceleration of change in temperature of the level-measuring thermistor 100, indicating an empty or not empty condition for the mixer, degasser and accumulator 46 (FIG. 3).

To provide a signal to the pump sending and control circuit 82 (FIG. 3) from the mixer sending circuit 84 (FIG. 3) (1) a conductor 210 electrically connects the mixer sensing circuit 84 (FIGS. 3 and 4) to the digital control unit 50 (FIG. 2); and (2) the digital control unit 50 (FIG. 2) is electrically connected to the mixer-sensing circuit 84. Signals are transmitted on conductor 210 to the digital control unit 50 in response to signals indicating an empty condition on conductorw 103A and 103B (indicated as 103 in FIG. 3).

For this purpose, the logic circuit includes five adjustable threshold amplifiers 104, 212, 214, 216 and 218, associated with five potentiometer circuits 132, 220, 222, 224 and 226, respectively, each connected to a NAND gate circuit 228 which, in turn, is connected to a transistor output circuit 230.

The differentiator 112 provides a negative going signal when there is a transition from dry to wet and positive going when wet to dry. When the unbalance and derivative signals are beyond the threshold set in the potentiometers 140, 220, 222, 224 and 226, the: (1) status circuit provides a signal; (2) first derivative comparators 212 and 218 provide negative going and positive going signals above the threshold for first derivative signals; and (3) second derivative and threshold amplifiers 216 and 214 providing negative going signals. All the threshold amplifiers except amplifier 104 sense derivative information and amplifier 104 senses status information.

To cause the threshold amplifier 104 to provide a negative going signal when the bridge 108 becomes unbalanced, the inverting terminal of amplifier 104 is electrically connected: (1) to electrical common through a 1 uf (microfarad) capacitor 128; (2) to the reference thermistor 102 through 1 M (megaohm) resistor 134, conductor 111 and the 33.2 K resistor 138 (FIG. 5) in series in the order named; (3) to the center tap 130 of potentiometer 132 through the resistor 134, and a 44.2 K resistor 136.

In this circuit, the potentiometer 132 has one end of its resistance 140 electrically connected to a source 142 of negative 12 volts and its other end electrically connected to a source 120 of a positive 12 volts to set a threshold on the inverting terminal of the threshold amplifer 104. The non-inverting input terminal of the threshold amplifer 104 is electrically connected to the ungrounded end of the level-measuring thermistor 100 through the 1 M resistor 144.

To cause the threshold amplifier 212 to provide a negative output signal upon receiving a negative going first threshold of an unbalance signal, the non-inverting input terminal of the amplifer 212 is electrically connected to conductor 150 to receive the first threshold and the inverting terminal is electrically connected to the center tap of the potentiometer 220. One end of potentiometer 220 is electrically connected to the source 120 of positive 12 volts and the other electrically connected to electrical common.

To cause the output of threshold amplifier 216 to provide a negative going output signal upon receiving a positive going second derivative potential, the inverting input input terminal of the threshold amplifier 216 is electrically connected to the output of the differentiating amplifier 200 and its non-inverting input terminal is electrically connected to its output through a 200 K feedback resistor 225 and to the center tap of the potentiometer 224. One end of the potentiometer 224 is connected to electrical common and its other end is connected to a source 120 of a positive 12 volts.

To cause the derivative amplifier 218 to provide a negative going signal upon receiving a negative going first derivative potential, the non-inverting input terminal of the derivative amplifier 218 is electrically connected to conductor 150 to receive the first derivative of an unbalance signal and its inverting terminal is electrically connected to the center tap of the potentiometer 226. One end of potentiometer 226 is connected to electrical common and its other end is connected to a source 120 of a positive 12 volts.

To cause the transistor 230 to provide a positive or negative signal to conductor 210 indicating an empty or not empty mixer, degasser and accumulator 46, respectively, the transistor 230 is an NPN transistor having: (1) its emitter connected to electrical common; (2) its collector connected to conductor 210 and to a source 170 of a positive 5 volts through a 4.7 K resistor 132; and (3) its base electrically connected to the output of the NAND gate 244 through a 100 K resistor 234.

To provide a negative going signal when the mixer, degasser and accumulator 46 becomes empty and a positive going signal when it becomes not empty, the NAND gate 244 has one input electrically connected to the output of NAND gate 240 and its other input electrically connected to the collector of the NPN transistor 248. The collector of the NPN transistor 248 is electrically connected to a source 120 through a 10 K resistor 250 and has its emitter connected to electrical common. The transistor 230 and the transistor 248 are both 3704 transistors.

To sense an empty condition, one input of the NAND gate 240 is electrically connected to the output of the threshold amplifier 104 to receive a positive signal indicating that the bridge 108 is unbalanced and its other input electrically connected to the output of the NAND gate 242, one input of which is electrically connected to the output of the threshold amplifier 212 to receive a positive going signal upon receiving a positive going first derivative potential and its other input electrically connected to the output of the threshold amplifier 214 to receive a negative going second derivative potential presence of a negative derivative of voltage on thermistor 100.

To provide a negative output to the base of transistor 248 upon sensing a not empty condition of the mixer, degasser and accumulator 46, the NAND gate 246 has its output electrically connected to the base of the NPN transistor 248 through a 100 K resistor 247, one rail electrically connected to a source 120 of a positive 12 volts, the other rail connected to electrical common, one input electrically connected to the output of the threshold amplifier 216 to detect a negative going signal indicating positive going second derivative of an unbalanced signal from the bridge 108; and its other input electrically connected to the output of the threshold amplifier 218 to receive a negative going transition indicating a positive derivative of the bridge signal upon the filling of the mixer, degasser and accumulator 46.

In operation of the mixer sensing circuit 84, the thermistor 102 which is mounted near the bottom of the mixer, degasser and accumulator 46 is maintained at a constant heated temperature by the insulating characteristic of the solvent which always covers it whereas the thermistor 100 warms when the fluid drops below it indicating an empty mixer, degasser and accumulator.

The thermistor 100 upon warming unbalances the bridge 108 to generate a negative going signal at the non-inverting input terminal of the threshold amplifier 104 and if large enough to overcome the positive signal set in the potentiometer 132 applies a positive going signal to the NAND gate 240 indicating an empty condition.

In FIG. 7, there is shown a schematic circuit diagram of the value sensing and control circuit 80 having a valve driven circuit 251, a first differentiating circuit 252, a second differentiating circuit 254, an output circuit 256 and a blocking circuit 258. The valve drive circuit 251 is electrically connected to the solenoid winding of the first valve and to the conductor transmitting a control signal to open the valve so as to receive signals indicating the open condition of the valve and is electrically connected to the first differentiator circuit 252 which differentiates the potential across the solenoid winding that opens the valve.

The second differentiating circuit 254 is electrically connected to receive the first derivative of the voltage across the relay winding and differentiate it to detect the motion of the solenoid plunger and transmit a signal to the output circuit. The output circuit receives a signal from the blocking circuit to clock signals representing the input turn-on signal for the valve and passes the second derivative as a signal indicating that the valve is opening.

A second valve is shown at 260 electrically connected to receive a potential from a solenoid winding on conductor 262 and a control turn-on signal on conductor 264 and transmit the signal 266 indicating that a second valve is open. There may also be a third control circuit connected in a similar manner to the second valve control circuit 260 as the second valve circuit 260 is connected to the first valve circuit shown in detail. The second and third valve circuits will have the same circuitry (not shown in FIG. 7) and operate in the same manner as the circuitry for the first valve to be described in greater detail hereinafter.

To generate a signal representing the opening of the first valve, the valve driver 251 includes an amplifier 270, a PNP transistor 272 and an NPN transistor 274. The amplifier 270 has its input electrically connected to a conductor 280 to receive a signal for opening the valve and has its output electrically connected to: (1) the base of the PNP 3702 transistor 272 through a 10 K resistor 282; (2) to a source of 284 of positive 26 volts through the resistor 282 and a 10 K resistor 286; (3) to the emitter of the transistor 272 through the resistors 282 and 286. The collector of the transistor 272 is electrically connected to the base of the transistor 274 through a 1.8 K resistor 288 and to the emitter of the transistor 274 through the resistor 288 and a 1 K resistor 290.

To provide valve drive, the transistor 274 has its collector electrically connected to: (1) the emitter of the transistor 272 through the forward resistance of a 1N5060 diode 292 and a 1 K resistor 294 in a series: and (2) to the valve pouwer source of positive 26 volts through the valve solenoid winding 296 for the first valve. Transistor 274 has its emitter electrically connected to conductor 300 and to a source 302 of a negative 26 volts through a 470 ohm resistor 304.

To form a first derivative, the first differentiating circuit 252 includes an RC differentiator 306 and an operational amplifier circuit 308. The differentiation circuit differentiates the signal from the solenoid and conducts it to the second differentiating circuit 254.

To differentiate the signal, the differention circuit 252 includes a 0.01 uf (microfarad) capacitor 310 and a 4.7 K resistor 312 connected in series between conductor 300 and the inverting terminal of the operational amplifier 308. One plate of the capacitor 310 and one end of the resistor 312 are electrically connected to electrical common through the forward resistance of a 1N914 diode 314 and the reverse resistance of a 1N914 diode 316 to provide rapid recovery from ceraloads.

The operational amplifier 308 is a conventional operational amplifier having a negative 12 volt rail 318 and a feedback circuit with a 100 K resistor 320 in parallel with a 0.001 uf capacitor 322. Its non-inverting input is grounded and its output is electrically connected to the second differentiating circuit 254 which is identical to the first differentiating circuit 252. The second circuit 254 provides the second derivative of the signal to the output circuit 256.

The output circuit 256 includes a 1N914 diode 330, 4050B buffer amplifier 332, and a NAND gate 334. The anode of the diode 330 is electrically connected to the output of the second differentiating circuit 254 to receive an input and the output of the NAND gate 334 is electrically connected to a conductor 336 to provide a signal indicating that the first valve is open. The cathode of the diode 330 is electrically connected to: (1) electrical common through a 22 K resistor 338; (2) electrical common through a 0.01 uf capacitor 340 and to the input of the amplifier 332. The amplifier 332 and the NAND gate 334 have a rail electrically connected to a source 170 of a positive 5 volts and to electrical common. The other input of the NAND gate 334 is electrically connected to the blocking circuit 258 which applies a signal to block an output during the time interval of the initial valve turn-on signal on conductor 280.

To provide a positive blocking signal against the initial turn-on signal applied to conductor 380, the blocking circuit 258 generates a positive pulse for application to the NAND gate 336. For that purpose, blocking circuit 258 is electrically connected to conductor 280 and has its output electrically connected to one of the inputs of the two input NAND gate 336. Its input is electrically connected: (1) to a source 170 of a positive 5 volts through the capacitor 350 and the forward resistance of a 1N914 diode 354 and to an input of the NAND gate 336 through the capacitor 350 and an amplifier 356.

In operation, the valve sensing and control circuit receives a valve opening signal from the solenoid when it opens and differentiates it for application to a NAND gate. The signal in response to electrical energization of the valve is blocked by the NAND gate so that only the signal due to movement of valve plunge is passed to indicate that the valve is opening. The signals at 336 from the second derivative indicate the time the valves start to open and the time they are fully opened. This time is used to correct the stored time of opening of valves to create the programmed gradient and thus correct for the individual times required by newly installed valves or for drifts in valve switching time from the time of the signal to switch. This sensing is accomplished using the effect of a change in inductance on d.c. current, resulting in a pulse applied from the coil 296 for the solenoid which operates the valve. To prevent cavitation, the pump is slowed in speed before the valves start opening, and slowly increased to a higher speed when the valves are fully opened.

Figure 8:
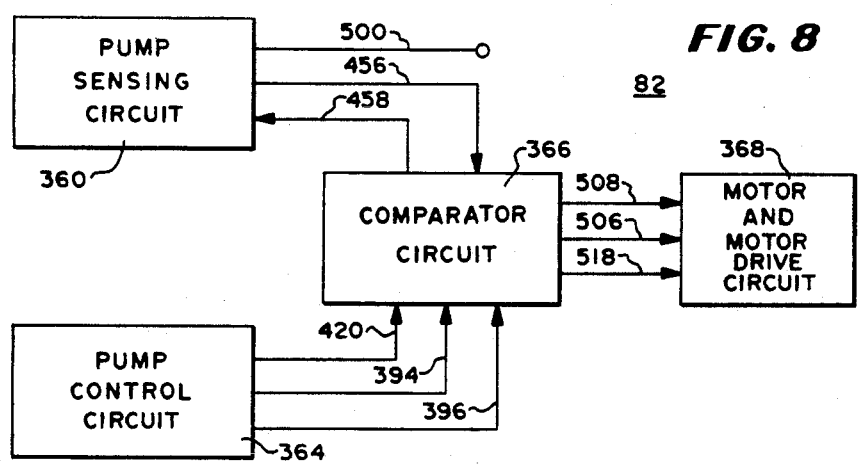
FIG. 8 is a block diagram of a portion of the embodiment of FIG. 3.

In FIG. 8, there is shown a block diagram of the pump sensing and control circuit 82 having a pump sensing circuit 360, a sensing circuit 362, a pump control circuit 364, a comparator circuit 366 and a motor and motor drive circuit 368. The pump sensing circuit 360 senses the piston position and piston movement and supply signals to the comparator circuit 366 and to the digital control circuit 50 (FIG. 2). The pump control circuit 364 supplies signals to the comparator circuit 366 indicating the desired motion of the pump pistor and the comparator circuit 366 supplies the signal to the motor and motor drive circuit 368 in response to the signals it receives from the pump sensing circuit 360 and from the pump control circuit 364 to control the speed of the motor through the motor and motor derive circuit 368. The center position of a refill stroke is sensed by the pump sensing circuit 360 and transmitted through conductor 500 to the digital control unit 50.

Figure 9:
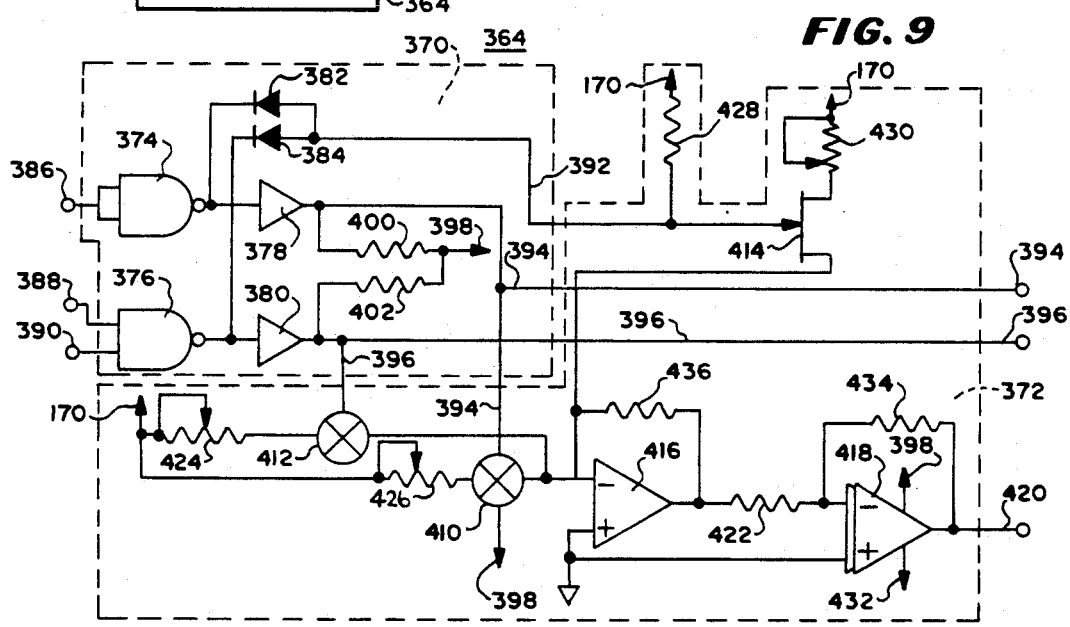
FIG. 9 is a schematic circuit diagram of a portion of the embodiment of FIG. 8.

In FIG. 9, there is shown a schematic circuit diagram of the motor control circuit 364 having a logic circuit 370 and a digital-to-analog converter 372. The logic circuit applies a code to the digital-to-analog converter which responds by applying voltages to the comparator circuit 366 (FIG. 8) which causes the motor and motor drive circuit 368 to stop, run at low speed, run at medium speed or run at fast speed.

To apply a coded output signal to the digital-to-analog converter 372, the logic circuit 370 includes first and second NAND gates 374 and 376, first and second diodes 382 and 384. The ouputs of the first and second NAND gates 374 and 376 are electrically connected to corresponding inputs of the first and second amplifiers 378 and 380 and to corresponding cathodes of the first and second diodes 382 and 384.

To control the motor speed, the NAND gate 374 has its inputs electrically connected to input conductor 386 and the NAND gate 376 has its two inputs electrically connected to conductors 388 to 390 respectively. The anodes of the first and second diodes 382 and 384 are electrically connected to a conductor 392 for application to the digital-to-analog converter 372 and the outputs of the first and second amplifiers 378 and 380 are electrically connected to conductors 394 and 396 respectively.

A source of 12 volts 398 is electrically connected through a first 10 K resistor 400 to the output of amplifier 378 and through a second 10 K resistor 402 to the output of amplifier 380. The first and second NAND gates 374 and 376 are types 7400, the first and second amplifiers 378 and 380 are types 7407 and the first and second diodes 382 and 384 are types 1N914.

In controlling the speed of the motor the output signals of the NAND gates 374 and 376 and cause the following results: (1) when the output of the first NAND gate 374 is a binary zero or low and the output of the NAND gate 376 is a binary zero or low, the motor is stopped; (2) when the output of the first NAND gate 374 is a binary one and the output of the NAND gate 376 is a binary zero of low, the motor is traveling at a slow speed; (3) when the output of the NAND gate 374 is a binary zero and the output of the secondary NAND gate 376 is a binary one, the motor is traveling at a medium speed and then the output of the first NAND gate 374 and the second NAND gate 376 are each a binary one, the motor is traveling fast. When both inputs to the NAND gates are positive, their outputs are low and with all other combinations their outputs are high.

To supply an analog motor drive circuit and a coded circuit for motor braking, the digital-to-analog converter 372 includes a first switch 410, a second switch 412, a MOSFET switch 414, a first operational amplifier 416 and a second operational amplifier 418. The outputs of the first and second switches 410 and 412 and of the MOSFET 414 are each electrically connected to the inverting terminal of the amplifier 416. The output of the amplifier 416 is electrically connected to the inverting terminal of the amplifier 418 through a 22 K resistor 422 and the output of the second derivative amplifier 418 is electrically connected through the analog-output conductor 420 to the comparator circuit 366 (FIG. 8).

To supply the proper voltages to the analog-output conductor 420, a source 170 of a positive 5 volts is electrically connected to the source of the switch 412 through a 50 K potentiometer 424 to the source of the switch 410 through a 250 K potentiometer 426, to the gate of MOSFET transistor 414 through a 47 K resistor 428 and to the source of the 2N7000 MOSFET 414 through a 50 K potentiometer 430.

The amplifiers 416 and 418 have their non-inverting input terminals connected to the electrical common and the second operational amplifier 418 has a source 120 of a positive 12 volts connected to one of its rails and a source 142 of a negative 12 volts connected to its negative rail. Each of them has a different one of the 22 K resistors 434 and 436 connected across it. The gate of MOSFET switch 414 is connected to conduit 392 to open it, the gate of the switch 410 is electrically connected to conductor 394 to open it and the gate of the switch 412 is electrically connected to conductor 396 to control it so as to apply stages of analog-output voltage to amplifiers 416 and 418 and then to the analog-output conductor 420.

Figure 10:
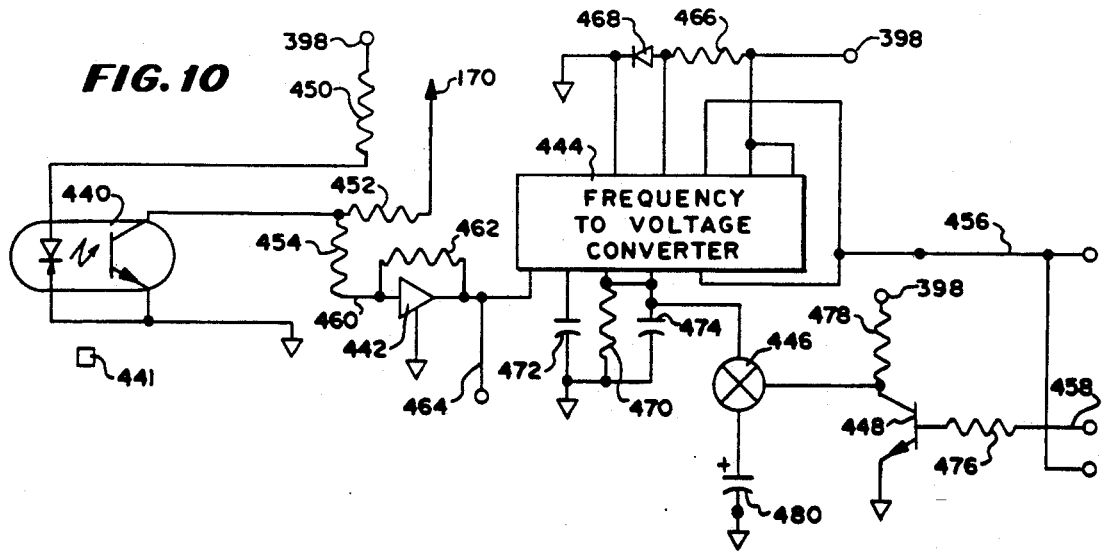
FIG. 10 is a schematic circuit diagram of another portion of the block diagram of FIG. 8.
Figure 11:
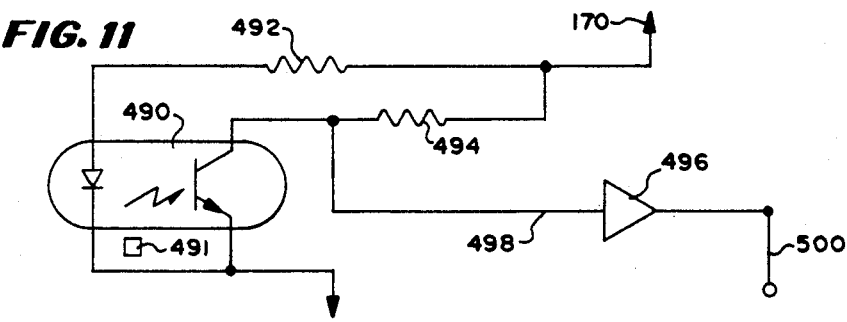
FIG. 11 is schematic circuit diagram of still another portion of the block diagram of FIG. 8.

In FIG. 10, there is shown a schematic circuit diagram of a portion of the pump sensing circuit 360 which generates an analog voltage representing the speed of the pump for application through conductor 456 to the comparator circuit 366. For this purpose, the pump sensing circuit 360 includes an optical sensor 440, a hysteresis amplifier 442, a frequency-to-voltage converter 444, an analog switch 446 and a NPN transistor 448. A second portion of the pump sensing circuit which generates a glas position for the mid-refill stroke of the piston is shown in FIG. 11.

The optical sensor 440 is electrically connected through the hysteresis amplifier 448 to the frequency-to-voltage converter 444 to which it applies pulses indicating the rate of movement of the piston in the pump for conversion to an analog-output voltage on conductor 456. The transistor 448 receives a signal on conductor 458 indicating a braking action and applies a signal through the switch 446 to terminate the output of the frequency-to-voltage converter 444 during a braking action.

To sense movement of the pump piston, an optical disc illustrated schematically at 441 is mounted to the shaft of the pump motor for rotation therewith through the light beam of the optical sensor 440 which senses the indicia and generates electrical pulses therefrom in a manner known in the art. For this purpose, a source 120 of a positive 12 volts is electrically connected through the 330 ohm resistor 450 to a light emitting diode within the optical sensor 440 to generate light for application through the sensing disc through a light-sensing element. The light sensing element is electrically connected to a source 170 of a positive 5 volts through the 1.2 K resistor 452 with the other elements of the light emitting diode and the light sensor being electrically connected to the electrical common of the circuit.

The output conductor 460 of the optical sensor is electrically connected to the input of the amplifier 442 which serves as a hysteresis amplifier. This amplifier has a 220 K feedback resistor 462 and has its output electrically connected to tachometer output conductor 464 and to the input of the frequency-to-voltage converter 444. The amplifier 442 is a type 4050 amplifier.

To generate an analog potential proportional to the frequency of input signals, the LM2907 frequency-to-voltage converter 444 has its output terminals electrically connected to conductor 456 and is biased by a source 120 of a positive 12 volts electrically connected to pins 9 and 8 and to pin 11 through a 10 K resistor 466 and to pin 12 through the forward resistance of a 1N914 diode 468 the cathode of which is also electrically connected to electrical common. The output of the switch 446 is electrically connected to pins 3 and 4 of the frequency-to-voltage converter 444 and to electrical common through a 100 K resistor 470. Pin 2 of the frequency-to-voltage converter 444 is electrically connected to electrical common through the 0.001 capacitor 472 and pin 4 is electrically connected to electrical common through the 0.05 microfarad capacitor 474.

To decrease the ripple of the analog voltage from conductor 456 when the motor is running slowly, the NPN transistor 448 is electrically connected through a 220 K resistor 476 to conductor 458 from the comparator circuit 366. The emitter of the NPN transistor 448 is electrically connected to electrical common and its collector is electrically connected to the source 120 of a positive 12 volts through a 10 K resistor 478 and to the gate of the switch 446 on pin 6. Pin 8 of switch 466 is electrically connected through the 1 MF capacitor 480 to electrical common. The switch 446 is a type of 4016 analog switch.

With this configuration, the optical sensor 440 senses indicia and generates pulses at a frequency proportional to the motor rotation speed for application to the hysteresis amplifier 442 to the input of the frequency-to-voltage converter 444. The frequency-to-voltage converter 444 converts the frequency to an analog potential proportional to it for application to the comparator circuit 366 through conductor 456.

In FIG. 11, there is shown another portion 362 of the pump sensing circuit 360 having a type 835A optical sensor 490, a 150 ohm resistor 492, a 47 K resistor 494 and a type 4050 amplifier 496. The optical sensor 490 detects a position flag 491 connected directly to the pump shaft to rotate with it and block light between the light emitting and light sensitive elements at dead center at the end of a delivery stroke of the pump. This element may also be a disc that rotates with the pump motor output shaft or an element attached directly to a reciprocating pump shaft to move linearly in line therewith.

To generate an electrical signal in response to the moving flag, the source 170 of a positive 5 volts is electrically connected: (1) to the one side of the light emitting element through the resistor 492, the other side being grounded to generate light; and (2) to the light sensing element through the resistor 494. The other terminal of the light sensing element is electrically connected to ground to generate a signal indicating the center point of the piston stroke on a conductor 498. Conductor 498 is electrically connected to the output conductor 500 through the amplifier 496 to provide a signal indicating the center point of a pump stroke. Conductor 500 is electrically connected to the digital control unit 50.

Figure 12:
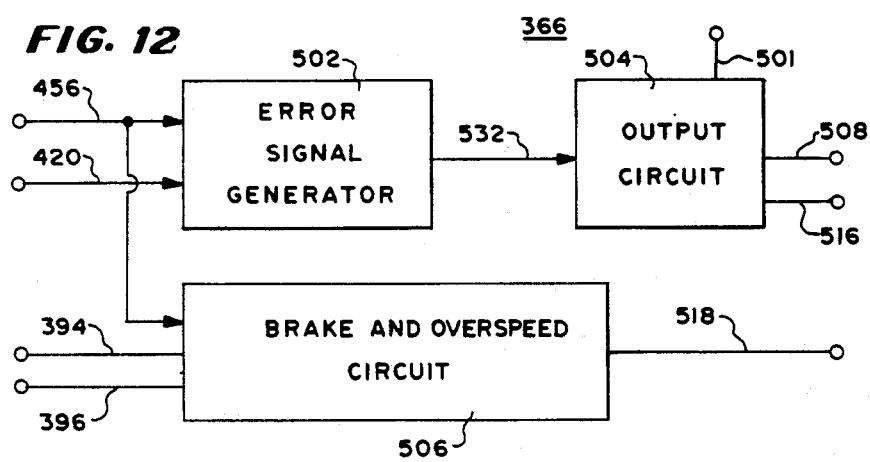
FIG. 12 is a block diagram of another portion of the block diagram of FIG. 8.

In FIG. 12, there is shown a block diagram of the comparator circuit 366 having an error signal generator 502, an output circuit 504 and a brake and overspeed circuit 506. The error signal generator 502 is electricaloly connected to conductors 456 and 420 to receive the analog signal representing pump speed from the pump sensing circuit 360 (FIG. 9 and FIG. 10) and the signal representing the programmed speed from the pump control circuit 364 (FIG. 8 and FIG. 9) and compares these two signals. It is electrically connected to the output circuit 504 and the brake and overspeed circuit to which it applies signals. The output circuit 504 is electrically connected to: (1) conductor 501 to receive a reset signal from the digital control unit (FIG. 2) to prevent the motor from operating during switching the main power to the gradient system; (2) conductor 508 to provide an output signal which controls the motor; and (3) to conductor 516 which provides overcurrent sensing for limiting the current to the motor.

The brake comparator 520 is overspeed circuit 506 and is electrically connected to conductor 456 to receive the analog speed circuit from the pump sensing circuit 360 (FIG. 8 and FIG. 10) and to conductors 394 and 396 through which it receives pump speed signals from the pump control circuit 364 (FIG. 8 and FIG. 9). Brake and overspeed circuit 506 applies an output signal on conductor 518 to slow or stop the motor, thus aiding in the changing of speed and stopping of the pump.

Figure 13:
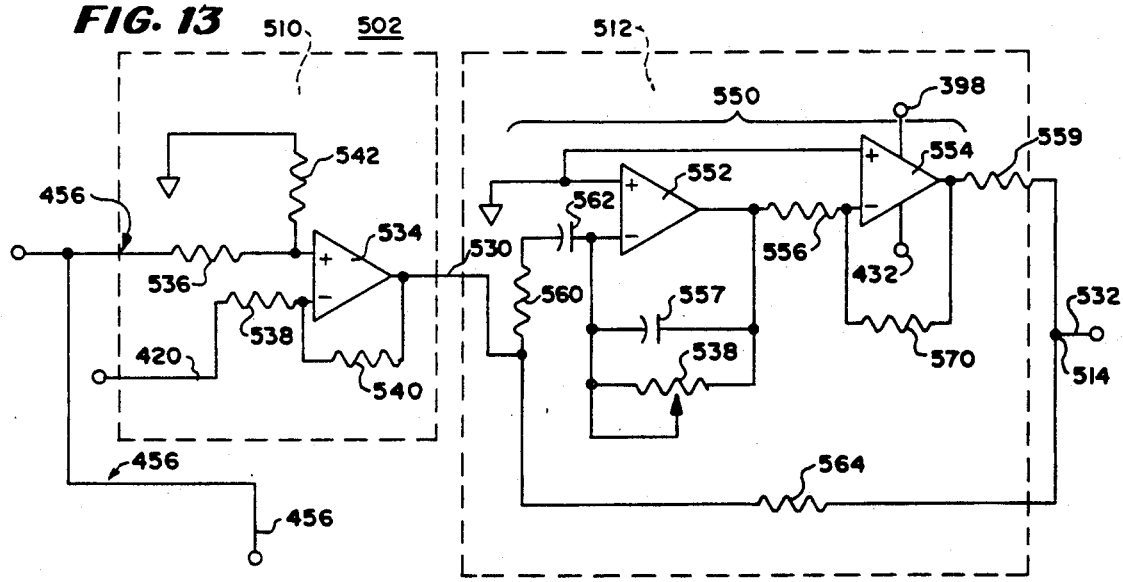
FIG. 13 is a schematic circuit diagram of a portion of the embodiment of FIG. 12.

In FIG. 13, there is shown a schematic circuit diagram of the error signal generator 502 having a speed comparison circuit shown generally at 510, a damping circuit shown generally at 512 and a summing node 514.

The speed comparison circuit 510 is electrically connected to conductor 456 to receive the analog speed signal from the pump sensing circuit 360 and to conductor 420 to receive the analog programmed speed signal from pump control circuit 364. It provides an output error signal on conductor 530 to damping circuit 512 which differentiates the signal and applies the differentiated signal and the original signal to summing node 514 to which it is connected. The summing node 514 provides the sum of the first differential and the error signal to the output circuit 504 (FIG. 12) through a conductor 532.

To compare the actual speed with the commanded speed and generate an error signal, the speed comparison circuit 510 includes a type LF 353 operational amplifier 534 and four 47 K resistors 536, 538, 540 and 542 respectively. The non-inverting input terminal of the amplifier 534 is electrically connected to electrical common through the resistor 542 and to conductor 456 through resistor 536. The inverting input terminal of the amplifier 534 is electrically connected to conductor 420 through resistor 538 and to output conductor 530 through the feedback resistor 540.

To differentiate the error signal received on conductor 530 from the speed comparison circuit 510, the damping circuit 512 includes a diffferentiator 550 composed of a first LF 353 amplifier 552 and a second LF 353 amplifier 554. The series connected resistor 560 and capacitor 562 are electrically connected at one end to the input conductor 530 and at the other end to amplifier 552 and the amplifier 552 is connected through a 47 K resistor 556 to amplifier 554. The amplifier 554 has its output electrically connected to the summing node 514 through a 22 K resistor 559.

To differentiate the signal received on conductor 530, the differentiator 550 includes a 15 K resistor 560 and a 0.1 uf capacitor 562 electrically connected in series in the order named between conductor 530 and the inverting input terminal of the amplifier 552. The amplifier 552 has its non-inverting input terminal connected to common ground and has its inverting terminal electrically connected to its output through: (1) a 0.05 uf capacitor 557; and (2) a 250 K potentiometer 558.

Conductor 530 is also electrically connected through a 22 K resistor 564 to summing node 514 to apply the attentuated error signal to the summing node for additional to the differentiated signal.

To invert the output signal from amplifier 552, the amplifier circuit 554 has its non-inverting input terminal electrically connected to electrical common, its rails connected to a source 120 of a positive 12 volts and to a source 142 of a negative 12 volts respectively, its inverting input terminal electrically connected to one end of 22 K resistor 558.

In FIG. 14, there is shown a schematic circuit diagram of the output circuit 504 which amplifies the error signal and provides a signal to the motor drive circuit 368 (FIG. 16). For this purpose, the output circuit 504 includes a 2N3704 NPN reset transistor 580, a type LF 353 error signal operational amplifier 353 and a 2N4061 motor overcurrent threshold sensing transistor 584.

To cause amplifier 582 to provide a signal to conductor 508 directly related to the error input signal on conductor 532 but affected by reset signal from transistor 580 if a reset signal is received on conductor 501 to which transistor 580 is connected, conductor 532 is electrically connected to the inverting input terminal of the amplifier 582, the emitter of transistor 580 and the collector and base of transistor 584. The signal on conductor 5165 is proportional to the motor current. To provide an output error signal on conductor 508 in response to a signal on conductor 532, the amplifier 582 has its inverting input terminal electrically connected to the emitter of transistor 580 and its output connected through a 470 K feedback resistor 586 to conductor 532 and to the collector of transistor 584. Its non-inverting input terminal is connected to electrical common.

A source 284 of a positive 26 volts provides one supply to amplifier 582 and the other supply is electrically connected to: (1) a source 432 of a negative 12 volts through the reverse impedance of a 1N5237B zener diode 590; and (2) electrical common through a 4.7 K resistor 592. The output of the amplifier 582 is electrically connected to conductor 508 through the forward resistance of a 1N914 diode 594 and to the feedback resistor 586.

To provide a reset signal to the amplifier 582, the transistor 580 has its collector electrically connected to a source 284 of a positive 26 volts through a 2.2 K resistor 596, its base electrically connected to a source 284 of a positive 26 volts through a 2.2 K resistor 596, its base electrically connected to the reset conductor 501, to the source 284 of a positive 26 volts through a 47 K resistor 598 and to electrical common through a 100 K resistor 600. To provide a current limiting signal from conductor 516, the PHP transistor 584 has its base and collector electrically connected to conductor 532 and its emitter connected to conductor 516.

In FIG. 15, there is shown a schematic circuit diagram of the brake and overspeed circuit 506 having an overspeed circuit 520 and a brake control circuit 522. The overspeed circuit 520 is electrically connected to conductor 456 to receive the analog signal representing the speed of the pump and is electrically connected to conductors 394 and 396 to receive a code indicating the programmed speed and it provides an output signal on conductor 458 to the comparator 366 (FIG. 8) indicating low speed condition of the motor as well as to the brake control circuit 522. The brake control circuit 552 receives signals indicating an overspeed condition from the overspeed circuit 520 and applies the signal to conductor 518 to reduce speed or stop the motor.

To generate a signal representing overspeed, the overspeed circuit 520 includes a 321 derivative amplifier 610, a first 4011 NAND gate 612, a second 4011 NAND gate 614 and a potentiometer 618. The potentiometer 618 establishes a potential which is applied to one input of the derivative amplifier 610 for comparison with the signal on conductor 456 indicating speed.

The output from the derivative amplifier is electrically connected to one input of the NAND gate 612, the other input being electrically connected for a logic signal to conductor 394. The output of the NAND gate 612 is electrically connected to conductor 458. NAND gate 614 has both of its input terminals electrically connected to conductor 396 and its output electrically connected to the brake circuit 522.

To compare the analog signal indicating speed with a reference level, the potentiometer 610 has one end connected to electrical ground and its other end connected to a source 170 of a positive 5 volts. The non-inverting input is electrically connected to the tap of the potentiometer 618 which is a 20 K potentiometer and to the non-inverting input of the derivative amplifier 610 through a 180 K hysteresis feedback resistor 620 so as to provide a logical low signal to one of the inputs of the NAND gate 612 if the speed is higher than the value set on the potentiometer 618 resulting in positive output signal on conductor 458 indicating an overspeed condition.

Because the other input of NAND gate 612 is electrically connected to conductor 394, a positive signal is conducted to conductor 458 if the code is for a medium or zero speed setpoint or when the output of amplifier 610 is low indicating the motor is running faster than low speed. NAND gate 614, because both of its inputs are electrically connected to conductor 396, provides a positive signal any time that a binary zero is provided by conductor 396 indicating that it is not at the high nor the medium speed set point.

To initiate braking action, the brake circuit 522 includes two type 4011 NAND gates 622 and 624, the 4016 switch 626 and the type 3704 NPN transistor 628. NAND gate 622 has one of its two inputs electrically connected to conductor 458 and its other electrically connected to the output of NAND gate 614 and its output electrically connected to both of the inputs of NAND gate 624. NAND gate 624 is electrically connected to a source 120 of a positive 12 volts and has its output electrically connected to the control gate of the switch 626.

The input of the switch 627 is electrically connected (1) the source 120 of a positive 12 volts through a 10 K resistor 630; and (2) to the collector of the transistor 628 through the resistor 630 and an 820 ohm resistor 632. The output terminal of the switch 627 is electrically connected to the base of transistor 628, to its emitter through a 10 K resistor 634. The emitter of the transistor 628 is electrically connected to conductor 518 to apply a signal to the motor drive circuits for braking action.

With this arrangement, signals are provided to the motor to provide dynamic braking upon receiving a signal for slow speed or stop and signals modulating the drive voltage are applied to maintain the pumping speed at the programmed rate.

In FIG. 16, there is shown a schematic circuit diagram of the motor and motor drive circuit 368 having a motor drive circuit 640, a motor 642, and a brake circuit 644, with the motor drive circuit 640 being electrically connected to conductors 516 and 518 to receive signals for slowing the pumping rate.

To receive an error signal for controlling the motor 642, the drive circuit 640 includes a type 2N3704 NPN transistor 650, a type 2N6292 NPN transistor 652, a 10 K resistor 654 and a 1 K resistor 656. To drive both transistors 650 and 652 to conduction, conductor 508 with the error signal is electrically connected to: (1) the base of transistor 650; (2) the emitter of transistor 650 through the resistor 654; (3) the base of transistor 652 through the emitter of transistor 654; and (4) to the emitter of transistor 652 through the resistors 654 and 656 in series.

The collectors of transistors 650 and 652 are each electrically connected to a source 284 of a positive 26 volts and the emitter of the transistor 652 is electrically connected to one end of the armature of motor 642 to drive this motor, the other end of the armature being electrically connected to electrical common through a 1 ohm, 2 watt resistor 608.

To permit dynamic braking, the braking circuit 644 includes a type 2N6292 NPN transistor 670, a 1 ohm 2 watt resistor 672, a 1 K resistor 674, a 0.1 UF capacitor 676 and 1N5060 diode 678. Conductor 518 is electrically connected to the base of transistor 670 and through resistor 674 to: (1) conductor 516; (2) the emitter of transistor 670; (3) resistor 608; (4) the anode of diode 678; (5) the first plate of capacitor 626; and (6) the second armature of motor 642.

The collector of transistor 644 is electrically connected through resistor 672 to: (1) the emitter of transistor 652; (2) the cathode of diode 678; (3) the second plate of capacitor 626; and (4) the armature of motor 642. With this arrangement, transistor 670 is driven to conduction by conductors 518 and 516, causing motor 642 to be dynamically braked by dissipating energy through the resistor 672 and otherwise to operate as a motor from the potential across the emitter of transistor 640 and conductor 516.

Figure 17:
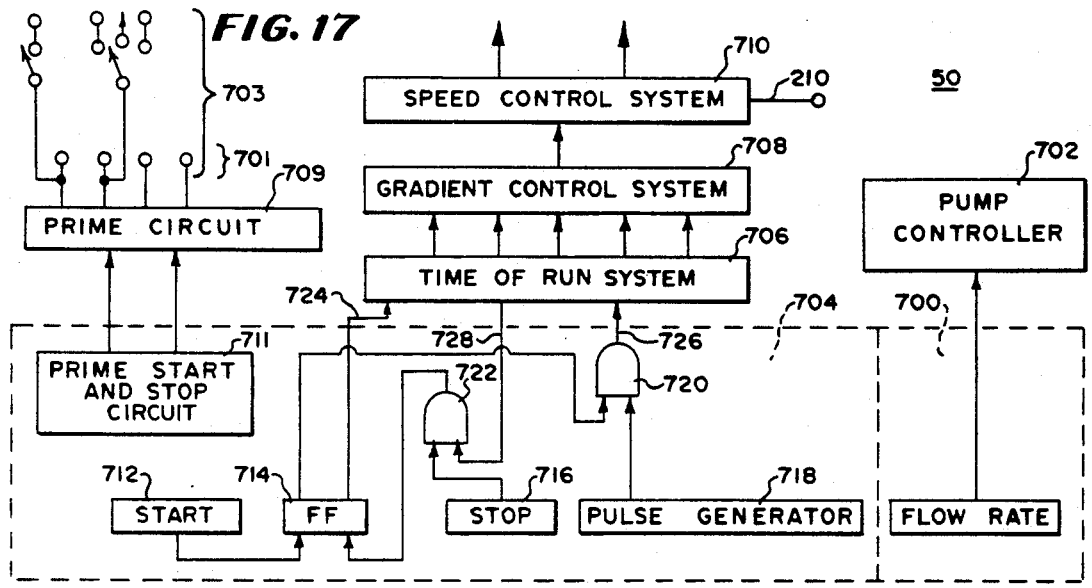
FIG. 17 is a block diagram of a portion of the embodiment of FIG. 2.

In FIG. 17, there is shown a block diagram of a portion of the digital control unit 50 (FIG. 2) having a flow rate control system 700, a pump controller 702, a chromatographic-run clock system 704, a time of run system 706, a gradient control system 708, a prime circuit 709, a prime start and stop circuit 711, and a speed control system 710. The prime start and stop circuit 711 contains the same circuit components and operator in the same manner as the chromatographic-run clock system 704 except it does not receive a reset line and does not contain a prime start and stop circuit of its own.

The flow rate control system 700 and the pump controller 702 are not part of this invention except insofar as they cooperate with the low pressure pumping and mixing system 24 (FIG. 1) and any suitable technique or circuit for permitting a chromatographer to set the flow rate through the chromatographic column may be employed. In the preferred embodiment, the flow rate system 700 and pump controller 702 are those of the co-pending patent application for chromatographic system assigned to the same assignee in the name of Robert W. Allington and filed concurrently herewith.

The chromatographic-run clock system 704 provides timing pulses for a fixed period of time and then terminates a chromatographic run unless programmed to repeat or manually repeat it. It is electrically connected to the time of run system 706 which selects segments programmed by time across the time period in the time of run system 706 which in turn is electrically connected to the gradient control system 708 which permits programming of the gradient between two or three solvents within each time segment selected and which is connected to the speed control system 710 which controls the timing of the low pressure pump 62 and the valve sensing and control circuit 80 to provide continuous eluent to the mixer, degasser and accumulator 46 (FIG. 2).

To provide basic timing for a continuous chromatographic run, the chromatographic-run system includes a start switch 712, a flip flop 714, a stop switch 716, a clock pulse generator 718, a AND gate 720, and an OR gate 722. The start switch 712 is electrically connected to the flip flop 714, the set output of which is connected to one of the two inputs to the AND gate 720, the other input being electrically connected to the ouput of the pulse generator 718. The stop switch 716 is electrically connected to one of the two inputs of the OR gate 722, the other input being electrically connected to the time of run system 706 which transmits the pulse at a time set within the time of run system 706.

To control timing of a chromatographic run, the output of the OR gate 722 is electrically connected to the reset input of the flip flop 714 and the output of the AND gate 720 to the clock pulse input of the time of run system 706 so that, upon pressing the start switch 712, the flip flop 714 is set, opening the AND gate 720 to clock pulses to begin timing and controlling a chromatographic run within the time of run system 706. The run continues until the end of the preset time period or until the stop switch 716 is closed, either of which cause the OR gate 722 to reset the flip flop 714 to terminate clock pulses and reset the time of run system 706.

The time of run system 706 periodically selects a segment of the gradient control system 708 which has been pre-programmed to supply a fixed mixture of solvents to the pump at times controlled by the speed control system 710 which is actuated by a demand signal on conductor 210 from the mixer sensing circuit 84 (FIG. 3).

To prime the pumps, the prime circuit 709 is started by depressing a key on the keyboard and continuously sends a code which causes solvents to flow (FIG. 3) and a signal to cause pump 62 to pump. The pump and switch 703 select valves 70 04 72 at each pump cycle to receive a turn-on signal. The low pressure pump thus continuously pumps until turned off and solvents A, B or C are pumped to flow into the mixer, degasser and accumulator 46, clearing the liner of air and causing it to overflow until the high pressure pump has been primed and begins pumping.

Figure 18:
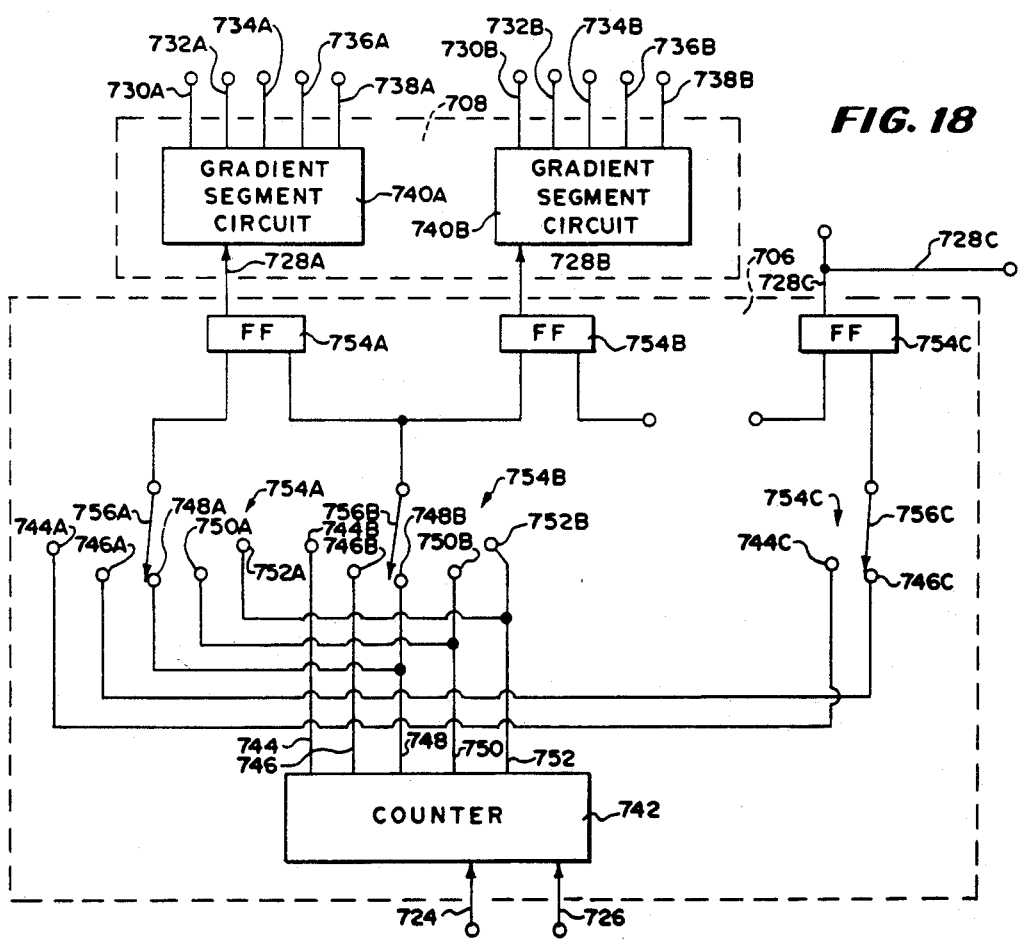
FIG. 18 is a block diagram of a portion of the embodiment of FIG. 17.

In FIG. 18, there is shown a schematic circuit diagram of several stages of the time of run system 706 and several stages of the gradient control system 708. The system as shown generally at 706 receives reset signals on conductor 724 from the reset output terminal of the flip flop 714 count signals on conductor 726 from the output of the AND gate 720 (FIG. 17) and applies an end of chromatographic run signal from the last stage selected for the chromatographic run through a conductor 728. This signal is applied through the OR gate 722 (FIG. 17) to the flip flop 714 (FIG. 17), terminating the run and resetting the time of run system 706.

The time of run system 706 includes a plurality of output conductors three of which are shown at 728A, 728B and 728C for illustrative purposes only although many more would normally be included. The output conductors 728A-728C are generally connected to units within the gradient control system 708 although 728C is shown connected through conductor 728 through the OR gate 722 (FIG. 17) to reset the flip flop 714 (FIG. 16). Any output may be selected for this purpose and controls the overall time of running of a chromatographic run.

To select individual segments of gradients, the gradient control system 708 includes a plurality of gradient segment circuits two of which are shown at 740A and 740B electrically connected to conductor 728A and 728B respectively for activation by the time of run system 706 at periodic, programmed intervals.

The gradient segment circuits each have a plurality of outputs which are programmed to be sequentially energized shown for example as 730A-738A for the gradient segment circuit 740A and 730B-738B for the gradient segment circuit 740B. There may be any number of gradient segment circuits even though even only two are shown for illustrative purposes and each may have any number of outputs such as those shown at 730A-738A so that the time of run system 706 selects at programmed intervals different gradient segment circuits which in turn sequence through a plurality of outputs in a programmed sequence.

To select certain ones of the outputs 728A, 728B and 728C or as many others as are desired, the time of run system 706 includes a counter 742 having a plurality of sequentially energized outputs, five of which are shown at 744, 746, 748, 750, and 752, for illustration although there may be any number of units. The time of run system 706 also includes a plurality of flip flops three of which are illustrated at 754A, 754B and 754C and a plurality of switching banks three of which are illustrated at 756A, 756B and 756C to correspond with gradient segment circuits and flip flops. In all of these cases there may be any number of units although three have been chosen for illustrative purposes.

Each of the switch banks 74A-74C (74C is shown in partial form) has a plurality of contacts each electrically connected to a different one of the outputs 744-752 of the counter 742 indicated by corresponding ones of the letters A, B, and C, so that the first bank has contacts 744A-752A and the second bank 744B-752B and so on. Each of the banks also has a corresponding switch arm or aperture 756A-756C.

The switch arms 756A-756C are each electrically connected to a different set terminal of a corresponding one of the flip flops 754A-754C and to the reset input terminal of the prior one of the flip flops so that switch arm 756B is connected to the reset input terminal of 754A. With this arrangement, the switch arms 756A-756C may be set at any place along the switching bank to cause its corresponding flip flop to be set. It thus selects a gradient segment circuit at a programmed time along the sequence of the counter 742 and together with the other switch banks forms a sequence by which the flip flops are set and reset. The switch arm for such banks sets a flip flops and resets the prior flip flop so that at programmed times output signals are applied to corresponding ones of the conductors 728A-728C in sequence.

Figure 19:
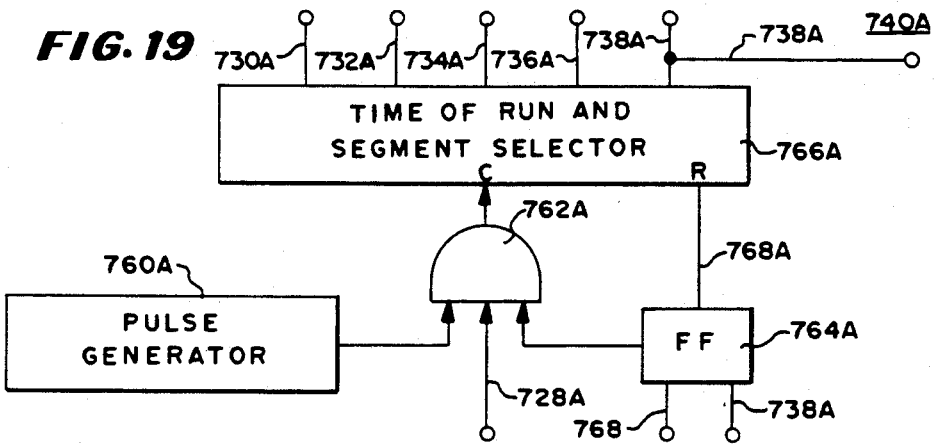
FIG. 19 is a block diagram of another portion of the embodiment of FIG. 17.

In FIG. 19, there is shown a schematic circuit diagram of one of the gradient segment circuits 740 having a pulse generator 760A, an AND gate 762A, a flip flop 764A and a time of run and segment selector 766A. The three input AND gate 762A has one of its three inputs electrically connected to the output of the pulse generator 760A to receive pulses at a frequency higher than that provided by the pulse generator 718 (FIG. 16), a second of its three inputs electrically connected to conductor 728A from the corresponding output of the time of run system 706 (FIG. 16) and the third of its outputs electrically connected to the set output of the flip flop 764A.

The set input of the flip flop 764A is electrically connected through conductor 768 to the digital output of the mixer sensing circuit 84 (FIG. 3) to sense an empty condition of mixer, degasser and accumulator 46 (FIG. 3) and set the flip flop 764 in accordance therewith. The output of the AND gate 762A is electrically connected to the time of run segment selector 766 so that when a demand signal is received, the particular one of the gradient segment circuits (in this case 740A) which is receiving a signal from the time of run system 706 receives count pulses in sequence through conductors 760A-738A.

The reset input terminal of the flip flop 764A is electrically connected to the last stage of the time of run segment selector 766A to receive a pulse resetting the flip flop 764A so as to terminate pulses to the time of run segment selector 766A and to reset a counter therein through conductor 768A.

The time of run and segment selector 766A is a circuit unit identical to the time of run system 706 programmed to provide a series of different signals the first one corresponding to the time of high speed pumping of the pump, the second to a time of low speed corresponding to when fluid from the first mixing valve is introduced, the next one being a time of high speed code, the following one being a time of low speed to receive still another fluid and the final one being a time of high speed resulting in a return forward pumping stroke to inject the two inserted fluids into the mixer.

After a forward stroke, the pump waits for another demand signal at which time it will go through another cycle filling itself with the proportion of liquids as controlled by the programmed selection of a particular gradient segment circuit, the proportion of each fluid being controlled by the programmed time of slow speed and valve opening.

Figure 20:
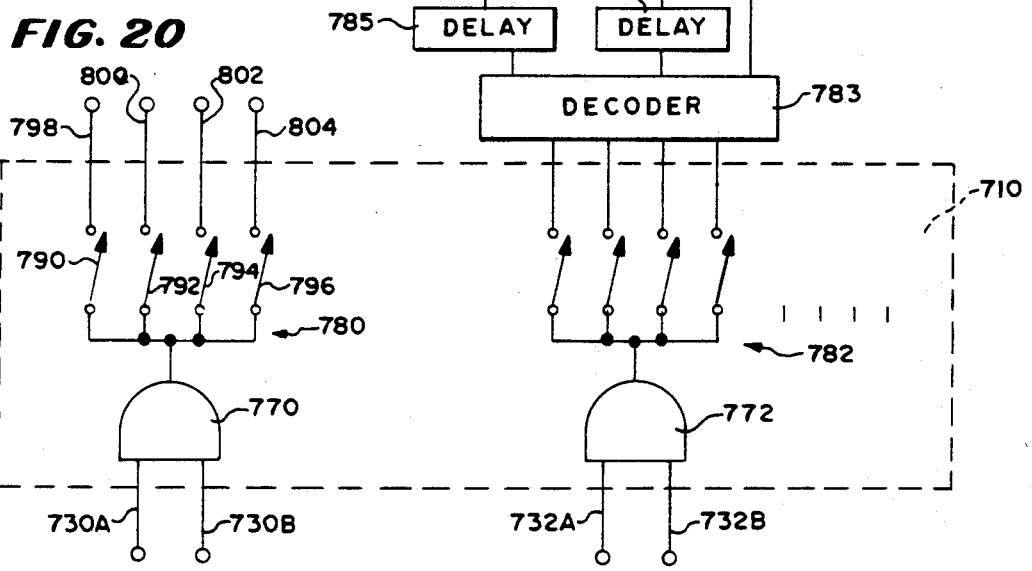
FIG. 20 is a schematic circuit diagram of still another portion of the embodiment of FIG. 17.

In FIG. 20, there is shown a schematic circuit diagram of the speed control system 710 showing two stages, one for the output conductors 730 and the other for the output conductors 732, each stage having a corresponding one of the OR gates 770-772 and there being many outputs as there are stages in each of the: (1) gradient segment circuits such as 740A (FIG. 17); (2)

gradient control system 708 (FIG. 16); and (3) programmable switch banks 780 and 782.

Each OR gate has a number of inputs corresponding to each of the gradient segment circuits with 730A and 730B being shown for illustration connected to OR gate 770 and with 732A and 732B shown for illustration connected to the OR gate 772. However, any number of inputs may be connected to one OR gate or an OR gate tree, if necessary, coming from a corresponding one of the gradient segment circuits such as 740A and 740B (FIG. 17).

The outputs of each of the OR gates such as 770 and 772 are electrically connected to a plurality of switch armatures in its corresponding one of the switching banks such as 780 and 782 respectively. Each of them includes four switches such as will be described in connection with the bank 780.

As illustrated with the bank 780, the output from the OR gate 770 is electrically connected to each of four switch armatures 790, 792, 794, and 796, each of which may be connected to a different one of the contacts 798, 800, 802, and 804, to provide a coded output signal under the control of the closed switches. The coded output signal indicates to the analog circuit the time of high speed travel, slow speed travel and valve opening and return stroke for filling the mixer, degasser and accumulator 46.

As described in connection with bank 782, a decoder 783 receives signals and generates signals to open valves and changes motor speed with preset delays and as in delay lines 785 and 787.

The time measured between time of energization of a valve and time of opening is recorded and the code for delay time set accordingly in the delays to increase motor speed only after the valve is open.

Figure 21:
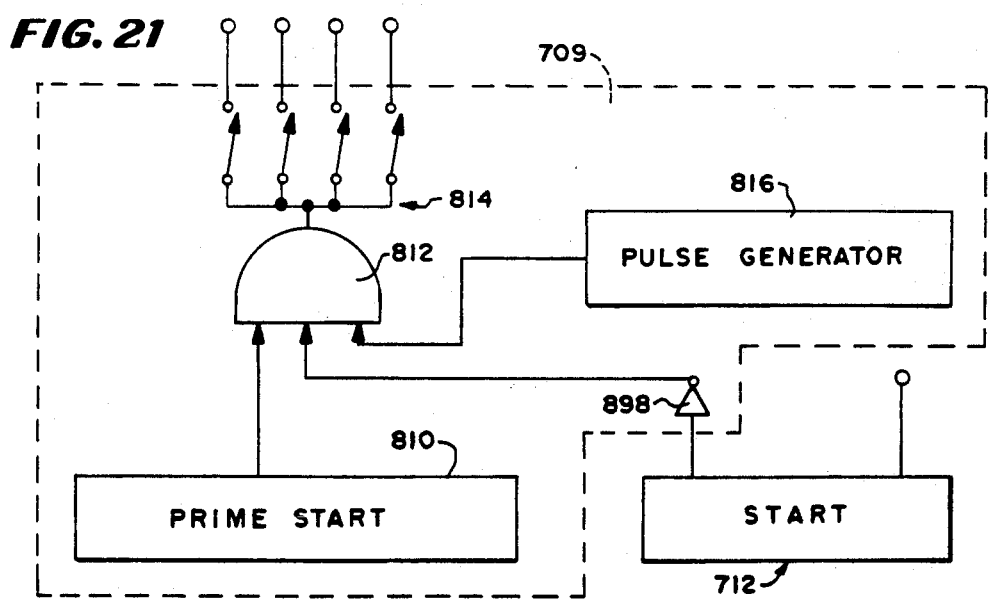
FIG. 21 is a schematic circuit diagram of still another portion of the embodiment of FIG. 17.

In FIG. 21, there is shown a prime circuit 709 having a prime start button on the keyboard, and AND gate 812, a switch bank 814 and a pulse generator 816. The prime start button 810 applies a pulse to the AND gate 812 in the same manner as the start button 712, which is to set a flip flop connected to its output. The start button 712 similarly applies an output such as that from flip flop 714 and to the AND gate 812, but such signal is inverted by an inverter 818 so that before the start button 712 is depressed to start a chromatographic run, a positive signal is applied to gate 812 so that when the prime start 810 is depressed and before the start button 712 (FIG. 17) is depressed, pulses from the pulse generator 816 are applied to the input of the AND gate 812 and result in an output signal to the switching bank 814.

The switching bank 814 is set in the same manner as the switching banks 780 and 782 (FIG. 20) but to a code to cause valves 70 and 72 to open, the pump 62 to operate and the pump in the high pressure pumping system 14 to operate until the start button 712 is depressed for the start of a chromatographic run. The chromatographic run is not started by the operator until solvent A is flowing through the system showing that the pumps have been primed and the column is ready to receive a sample by being stabilized with solvent A flowing through it at a stable pressure and constant preset flow rate.

While a proposed hardware circuit has been shown as part of the digital control unit 50, in the preferred embodiment the unit is partly software and partly hardware. An Intel P803AH computer is programmed with a Texas Instruments keypad and appropriate software to generate the digital signals controlling the valve and the low pressure pump. The software program relevant to these functions is summarized below and then given in full and contains a program to perform the same functions as shown in the proposed hardware schematics.

The program waits in the RUN-MOD procedure line 1187 until the mixer is empty. If it is empty, the program goes to line 1260. Here the subroutine Fill is called to fill the pump. Next, subroutine pump is called to empty the pump into the mixing chamber. If the HPLC flow rate is less than approximately 5 ml/min., the unit waits until the chamber is empty, then fills the pump and pumps into the chamber, at flow rates greater than 5 ml/min. the pump is immediately refilled after the pump stroke. This eliminates delay from the time the mixer signal arrives, and when the pump delivers the fluid.

In FILL, the program continually reads the angular location of the motor to determine if it is time to change motor speeds or activate one of the solenoid valves. Once a valve has been activated, the program also detects the valve switching signal. When the switching is detected, the delay is calculated as a function of motor displacement. This value is the amount of correction used when determining the switching point of the valve during the next pump stroke.

The program then goes to PUMP which monitors the unit during fluid delivery.

```
1151 2    FILL: PROCEDURE
1152 2        DECLARE LOCATION WORD;
1153 2        DECLARE (V1, V2, V3, V4) BIT;
1154 2        V1, V2=0;
1155 2        V3, V4=1;
1156 3        IF SWITCH 2 = 0 THEN DO;
1158 3            VALVE 1, VALVE 2 = 0;
1159 3            VALL TIME (100);
1160 3            END;
1161 3        ELSE IF SWITCH 1 = 0 THEN DO;
1163 3            VALVE 1 = 0;
1164 3            CALL TIME (100);
1165 3            END;
1166 2        IF SWITCH 1 ) 200 THEN CALL FAST;
1168 2        ELSE CALL SLOW;
1169 2        CALL TIME (OFF);
1170 2        LOCATION = TACH;
1171 3        DO WHILE LOCATION (SLOW 1);
1172 3            LOCATION = TACH;
1173 3            END;
1174 2        CALL SLOW;
1175 2    LOOP: LOCATION = TACH;
1176 3        IF (LOCATION ) SWITCH 1) AND V3
                 THEN DO;
1178 3            VALVE 1 = 0;
1179 3            V1 = 1;
1180 3            V3 = 0;
1181 3            END;
1182 3        IF (LOCATION ) SWITCH 2) AND V4
                 THEN DO;
1184 3            VALVE 2 = 0;
1185 3            V2 = 1;
1186 3            V4 = 0;
1187 3            END;
1188 3        IF VI AND (NOT V CHECK 1) THEN DO;
1190 3            V1 = 0;
1191 3            ERR 1 = LOCATION - SWITCH 1;
1192 3            END;
1193 3        IF V2 AND (NOT V CHECK 2) THEN DO;
1195 3            V2 = 0;
1196 3            ERR 2 = LOCATION - SWITCH 2;
1197 3            END;
1198 2        IF (LOCATION) SWITCH 1 + 15) AND
                 (LOCATION (SLOW 2) THEN CALL
                 FAST;
1190 2        IF (LOCATION SLOW 2) AND
                 (LOCATION ((SWITCH 2 + 15)) THEN
                 CALL SLOW;
```

-continued

| | | |
|---|---|---|
| 1193 | 2 | IF (LOCATION) SWITCH 2 + 15) THEN CALL FAST; |
| 1194 | 3 | IF LOCATION ) = 2183 THEN DO; |
| 1196 | 3 | CALL FAST; |
| 1197 | 3 | VALVE 1, VALVE 2 = 1; |
| 1108 | 3 | RETURN; |
| 1109 | 3 | END; |
| 1110 | 3 | IF ((CHAMBER AND 20H) () 20H) THEN DO; |
| 1112 | 3 | P15 = 1; |
| 1113 | 3 | SECONDS = 0; |
| 1114 | 3 | TENTH SEC = 0; |
| 1115 | 3 | I = 0; |
| 1116 | 3 | HFLAG = 0; |
| 1117 | 3 | LED = 14H; |
| 1118 | 3 | TSTART, TEND = 0; |
| 1119 | 3 | ACON, AP = SEGMENT (0).SA; |
| 1120 | 3 | BCON, BF = SEGMENT (0).SB; |
| 1121 | 3 | OPERATE = OAAH; |
| 1122 | 3 | CALL CHECKMEM; |
| 1123 | 3 | END; |
| 1124 | 3 | IF MSG THEN DO; |
| 1126 | 3 | CALL MOVCX0(.('B 98', CR),750,5); |
| 1127 | 3 | MSG = O; |
| 1128 | 3 | SBUF = TBUFFER(0) OR 80H; |
| 1129 | 3 | RBUFFPTR = 0; |
| 1130 | 3 | END; |
| 1131 | 2 | GOTO LOOP; |
| 1132 | 1 | END FILL; |
| 1133 | 2 | PUMP: PROCEDURE; |
| 1134 | 2 | .DECLARE ADUMMY WORD; |
| 1135 | 2 | DECLARE RFLAG BIT; |
| | | /* GO FASTER DURING DISCHARGE */ |
| 1136 | 2 | P13,P35 = 0; |
| 1137 | 2 | PDUMMY = 0; |
| 1138 | 2 | CALL CALC; |
| 1139 | 3 | DO WHILE PDUMMY (4150; |
| 1140 | 4 | IF ((CHAMBER AND 20H) () 20H) THEN DO |
| 1142 | 4 | P15 = 1; |
| 1143 | 4 | SECONDS = 0; |
| 1144 | 4 | TENTHSEC = 0; |
| 1145 | 4 | I = 0; |
| 1146 | 4 | HFLAG = 0; |
| 1147 | 4 | LED = 14H; |
| 1148 | 4 | OPERATE = 0AAH; |
| 1149 | 4 | TSTART, TEND = 0; |
| 1150 | 4 | ACON, AF = SEGMENT (0).SA; |
| 1151 | 4 | BCON, BF = SEGMENT (0).SB; |
| 1152 | 4 | CALL CHECKMEM; |
| 1153 | 4 | END; |
| 1154 | 3 | PDUMMY = TACH; |
| 1155 | 4 | IF MSG THEN DO; |
| 1157 | 4 | CALL MOVCX0(.('B98',CR),750,5); |
| 1158 | 4 | MSG = 0; |
| 1159 | 4 | SBUF = TBUFFER(0) OR 80H; |
| 1160 | 4 | RBUFFPTR = 0; |
| 1161 | 4 | END; |
| 1162 | 3 | END; |
| 1163 | 2 | CALL SLOW; |
| 1164 | 3 | DO WHILE NOT TDC; |
| 1165 | 3 | END; |
| 1166 | 2 | CALL RESET_TACH; |
| 1167 | 2 | P13,P35 = 1; |
| 1168 | 2 | CALL TIME (OFFH); |
| 1169 | 1 | END PUMP |
| 1170 | 2 | RUN MOD: PROCEDURE; |
| 1171 | 2 | DECLARE (DUM,J) BYTE; |
| 1172 | 2 | DECLARE CATCH BIT; |
| 1173 | 2 | FILLTIME = 40; |
| 1174 | 2 | XFILL = 0; |
| 1175 | 2 | LED = 14H; |
| 1176 | 2 | IF HFLAG THEN LED = 94H |
| | | /* FOR POWERUP */ |
| 1178 | 2 | CALL CHECKMEM; |
| 1179 | 2 | I=O; |
| 1180 | 2 | TSTART, TEND = 0' |
| 1181 | 2 | ACON,AF=SEGMENT (0).SA; |
| 1182 | 2 | BCON,BF-SEGMENT (0).SB; |
| 1183 | 3 | DO WHILE NOT TDC; |
| 1184 | 3 | END; |
| 1185 | 2 | P16 = 1; |
| 1186 | 2 | CALL RESET_TACH; |
| 1187 | 3 | TAG1: DO WHILE ((CHAMBER AND 40H) = 0) AND (NOT CHRRDY) AND (NOT M |
| 1188 | 3 | CALL CALC; |
| 1189 | 3 | CALL UPDATE; |
| 1190 | 4 | IF ((CHAMBER AND 20H) () 20H) THEN DO; |
| 1192 | 4 | P15 = 1; |
| 1193 | 4 | SECONDS = 0; |
| 1194 | 4 | TENTHSEC = 0; |
| 1195 | 4 | I = 0; |
| 1196 | 4 | HFLAG = 0; |
| 1197 | 4 | LED = 14H; |
| 1198 | 4 | OPERATE = 0AAH; |
| 1199 | 4 | TSTART, TEND = 0; |
| 1200 | 4 | ACON, AF = SEGMENT (0).SA; |
| 1201 | 4 | BCON, BF = SEGMENT (0).SB; |
| 1202 | 4 | CALL CHECKMEM; |
| 1203 | 4 | END; |
| 1204 | 3 | END; |
| 1205 | 3 | IF (CHRRDY OR MSG) THEN DO; |
| 1207 | 3 | IF CHRRDY THEN DUM=KEYBD; |
| 1208 | 3 | ELSE DUM = SERRPLY; |
| 1209 | 3 | |
| 1210 | 4 | IF NOT HFLAG THEN DO; |
| 1212 | 5 | IF DUM = HOLD THEN DO; |
| 1214 | 5 | LED = 94H |
| 1215 | 5 | CALL UPDATE; |
| 1216 | 5 | HGLAF = 1; |
| 1217 | 5 | OPERATE = 0ACH; |
| 1218 | 5 | CALL CHECKMEM; |
| 1219 | 5 | END; |
| 1220 | 5 | ELSE IF DUM = STOP THEN DO; |
| 1222 | 5 | BEEP_CON = 36H; |
| 1223 | 5 | ACON = 100; |
| 1224 | 5 | BCON = 0; |
| 1225 | 5 | RETURN; |
| 1226 | 5 | END; |
| 1227 | 4 | ELSE IF (DUM () NUL) THEN CALL BADKEY; |
| 1229 | 4 | END; |
| 1230 | 4 | ELSE IF (DUM = RUN) OR (DUM = HOLD) THEN DO; |
| 1232 | 5 | IF MFLAG THEN DO; |
| 1234 | 5 | SECONDS = 0; |
| 1235 | 5 | P15 = 1; |
| 1236 | 5 | I = 0; |
| 1237 | 5 | TSTART, TEND = 0; |
| 1238 | 5 | ACON, AF = SEGMENT (0).SA; |
| 1239 | 5 | BCON, BF = SEGMENT (0).SB; |
| 1240 | 5 | END; |
| 1241 | 4 | HFLAG = 0; |
| 1242 | 4 | TENTHSEC = 0; |
| 1243 | 4 | LED = 14H; |
| 1244 | 4 | CALL UPDATE; |
| 1245 | 4 | OPERATE = 0AAH; |
| 1246 | 4 | CALL CHECKMEM; |
| 1247 | 4 | END; |
| 1248 | 4 | ELSE IF DUM = STOP THEN DO; |
| 1250 | 4 | BEEP_CON = 36H; |
| 1251 | 4 | OPERATE = 0; |
| 1252 | 4 | ACON = 100; |
| 1253 | 4 | BCON = 0; |
| 1254 | 4 | RETURN; |
| 1255 | 4 | END; |
| 1256 | 3 | ELSE IF (DUM () 0) THEN CALL BADKEY; |
| 1258 | 3 | GOTO TAG1; |
| 1259 | 3 | END; |
| 1260 | 2 | IF XFILL THEN XFILL = 0; |
| 1262 | 2 | ELSE CALL FILL; |
| 1263 | 2 | CALL PUMP; |
| 1264 | 3 | IF (FILLTIME ( 30) THEN DO; |
| 1266 | 3 | FILLTIME = 0; |
| 1267 | 3 | CALL FILL; |
| 1268 | 3 | P13, P35 = 1; |
| 1269 | 3 | XFILL = 1; |
| 1270 | 3 | END; |
| 1271 | 3 | ELSE DO J = 1 TO 20; |
| 1272 | 3 | FILLTIME = 0; |
| 1273 | 3 | CALL TIME (OFFH); |

```
-continued
1274 3           END;
1275 2           CALL UPDATE;
1276 2           GOTO TAG1;
1277 1      END RUN_MOD;
1278 1      START: DISABLE;
1279 1           TACH_CON = 10110000B;
1280 1           TMOD - 100110B;
1281 2           IF (CHAMBER AND 4) () 4 THEN DO;
                 /* 19.2 KBAUD */
1283 2                TH1 = OHDH;
1284 2                PCON = 80H;
1285 2                END;
1286 2           ELSE DO;
                 /* 1200 BAUD */
1287 2                TH1 = 0E8H;
1288 2                PCON = 0;
1289 2                END;
```

Figure 22:
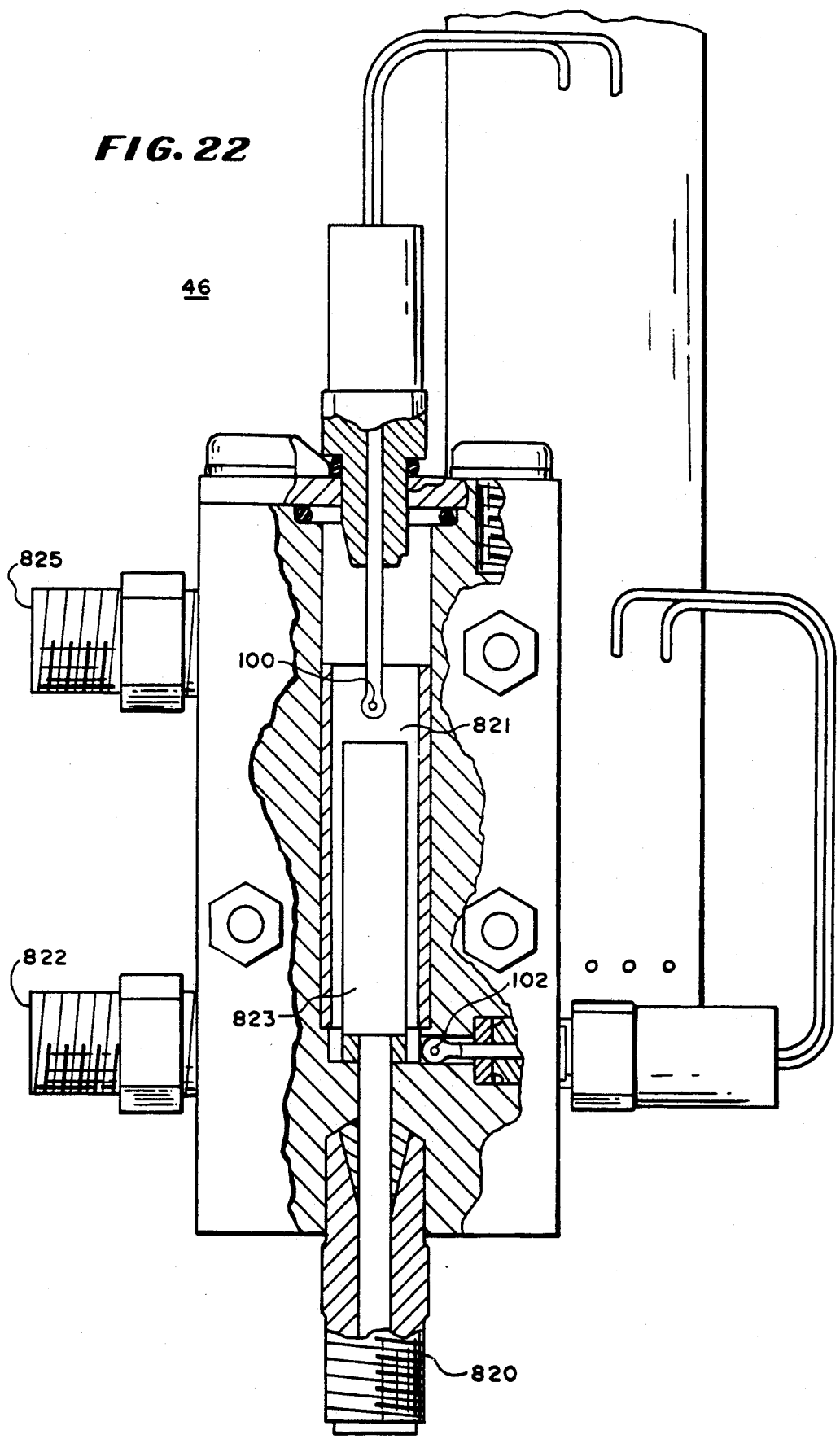
FIG. 22 is a sectional view of a portion of the embodiment of FIG. 2.

In FIG. 22, there is shown a fragmentary, elevational view, partly broken away in section of the mixer, degasser and accumulator 46, having a mixing chamber 823 within a column of porous frit, an influent inlet 820, an effluent outlet 822, a reference thermistor 102 and a level thermistor 100.

The mixing chamber 823 has a volume greater than that of the high pressure pumps cylinder so that the high pressure pump may receive fluid from conduct 822 on a fill stroke sufficient to fill its chamber. The volume of the accumulator 46 available to hold liquid should be small enough to permit a new mixture to change the ratio resident in it as rapidly as possible and maintain in it after filling the chamber of the high-pressure pump at least one percent of its full volume of liquid. It must be large enough for degassing. Its actual volumetric capacity is determined by the pump with which it cooperates and is generally between 0.25 ml and 500 ml.

The column of frit is hollow to form the mixing chamber 823 and receives fluid from the inlet 820 into its interior between the inlet 820 and outlet 822 so that the influent must flow through the frit which serves as a tortuous path and flow spreader before reaching the outlet. The fluid is injected into the hollow interior of the frit where it is mixed by the momentum of its insertion mass and velocity and then flows through the small pores of the frit to cause further mixing and removal of gases. The surfaces of the frit are of a material and area to cause nucleation, and in one embodiment are stainless steel with a pore size of 20 micrometers.

The frit should be spaced from the walls of the mixer enough so that even with the largest flow rate, they have time and space to form on the frit, to be removed from the frit by sol vent flow, and float to the top 821 of the mixer for removal through a vent 825 rather than being carried to the outlet for the solvent. The outlet is lower than the vent and below the surface of this solvent. With this arrangement, no helium gas sparging the solvent supply is necessary. The spacing from the walls must be at least 0.25 millimeter.

In the preferred embodiment, the frit is cup shaped resting on the bottom by a small cylindrical area. There is substantially no frit or other material besides liquid between the frit, the side walls and the top. The frit must have pores of a size between 2 and 20 microns in diameter.

The outlet of the mixer may be connected to any type of pump having suitable displacement volume. Thus, it may accommodate different makes, pressures, speeds of pumping and the like.

The reference thermistor 102 is mounted adjacent to the bottom of the mixing chamber 823 so that as long as there is fluid in the mixing chamber 823, it be covered and will retain heat whereas the level thermistor 100 will be uncovered upon emptying of the mixing chamber 823 and covered when it is filled. Liquid is pumped into the chamber by the low pressure pump where it degasses against the frit.

In summary, the gradient is programmed within the system controller 22 in a digital format and the high pressure pumping system 14 is primed. After priming, the high pressure pumping system pumps at its preset flow rate, emptying the mixer, degasser and accumulator 46 (FIG. 2). When the mixer, degasser and accumulator 46 is filled, it sends a signal to the analog control circuit 40 (FIG. 2) which causes the low pressure pump, valve and motor assembly 42 (FIG. 2) to refill the mixer by filling the pump with the programmed gradient in use at that time and pumping it into the mixer.

To program the gradient, up to nine segments each relating to a different mixture of solvents may be keyed into the keyboard 52 (FIG. 2) to establish a digital representation of the up to nine solvent mixtures to be used across the time of the chromatographic run. The flow rate may also be introduced.

In the embodiment of FIGS. 17-21, the time of the chromatographic run and the shape of the segments may be set by selecting the: (1) particular outputs of counter 742 (FIG. 18) to select the time up to reset; (2) by selecting particular outputs of the counter 742 to move from segment (such as 740A or 740B) within the switches (such as 754 A or 754B) to select the segment; and (3) setting within segments by the switches within the time of run and segment selector 766 (FIG. 19), valve opening times for the valves containing solvents to introduce solvent into the pump chamber as the pump is filling and thus control the proportions of mixtures.

To prime the high pressure pump, a signal is continuously applied from the keyboard to valves 70 and 72 causing fluid to flow into the pump 62 during each cycle and the demand signal is continuously applied to the low pressure pump to cause continuous pumping until pumping is observed from the high pressure pump, after which time, the signals are manually released. The flow rate may be set in a conventional manner and is not part of this invention, the setting being applied directly to the high pressure pump.

To provide a proper mixture of solvents to the mixer, degasser and accumulator 46 (FIGS. 2, 3 and 22), the sensing circuit 92 senses when the liquid in the mixer, degasser and accumulator 46 drops below one of two thermistors indicating an empty condition and transmits signals to the unbalance signal and first derivative circuit 94, and logic which generates a signal to an output logic circuit and to a second derivative circuit 98 which initiates a pumping and valve command to obtain more solvent in the mixer. The signals are compensated by the temperature compensation circuit 90 connected to the unbalance signal and first derivative circuit 94.

When an empty signal is sensed by the ANDing of the first and second derivatives or the unbalance signal between thermistors alone, the signals are applied to a logic circuit which begins a refill cycle. During the refill cycle, the programmed gradient is incorporated into the pump during the fill portion of the pump 62 as the pump is drawn back.

During the fill stroke, a valve port to one of the solvents is open to enable fluid to flow into the pump cylinder while the pump is operated at medium rate sufficiently slow to avoid cavitation. It is slowed further after the system controller 22 indicates that an amount less than the proper amount has been introduced. The first valve closes its first part and opens its second while the pump is moving slowly. When the valve opening is sensed, the pump speed is increased as soon as the valve transition is sensed by a circuit indicating it is opening. It is slowed after the system controller 22 indicates somewhat less than the proper amount of that solvent has been introduced.

As the first valve closes, the pump speed is slowed and when closed, a valve to the second solvent is opened while the pump is moving slowly. When the valve is fully opened, it is sensed and a signal applied to increase the return pump speed until the programmed amount of the second solvent has been introduced.

This process can be repeated for a third solvent in the preferred embodiment but with minor modifications any number of solvents may be employed.

Once the pump has been filled with the proper mixture of solvents, the foward stroke begins to introduce the solvent at a high rate to rapidly introduce the solvent into the mixer, degasser and accumulator 46 so that proper mixing takes place from the hydrodysiosis forces.

In the operation of the valves, there is a delay between when the valve is snergized and the plunger begins to move. In general, this time is not reliably constant. The system controller stores the time between when the valve is energized and the plunger begins to move. This time is stored and used to correct the lead time between energization and the valve port switching time for the next valve switching cycle, so that the plunger moves at the proper time to insure accuracy in solvent composition.

In the preferred embodiment, the valves are 3-way solenoid 161K031A valves manufactured and sold by Neptune Research, Inc., having offices at 481 Gleasondale Road, Stow, Mass. 01775, with all orifices bored to 40 thousandths diameter to prevent unfavorable pressure drops.

As can be understood from the above description, the chromatographic system 10 of this invention has several advantages: (1) the mixing efficiency of the system is independent of the flow rate of the high pressure pump that is supplied with solvents by the gradient programmer; (2) the gradient programmer is able to prime the high pressure pump; (3) the gradient programmer is able to mix several solvents with precision even though some of the solvents may be a low proportion of the mixture; (4) it is economical; and (5) it degasses the mixed solvent.

Although a preferred embodiment of the invention has been described in some detail, many modifications and variations are possible in the preferred embodiment without deviating from the invention. Accordingly, it is to be understood, that, within the scope of the appended claims, the invention may be practiced other than as specifically described.

We claim:

1. A gradient former adapted to supply gradient to a replaceable pump comprising:
    gradient pump means having a pump cycle and a refill cycle for pumping liquid;
    said gradient pump means having inlet valve means for providing a variable size flow opening for liquid entering said gradient pump means;
    reservoir means for receiving liquid from said gradient pump, storing it and supplying it to said replaceable pump; and
    means for controlling the pressure difference that forces liquid into said gradient pump means so that it is related to the size flow opening for liquid so liquid enters said gradient pump means without cavitation.

2. A gradient former according to claim 1 in which said means for controlling the pressure difference that forces liquid into said gradient pump without cavitation includes means for controlling the speed of the gradient pump means as it draws liquid during a refill cycle at a rate to avoid cavitation.

3. A gradient former in accordance with claim 2 in which said means for controlling the speed includes means for slowing the speed of said gradient pump down at the beginning of liquid entrance into said gradient and smoothly speeding up the gradient pump as said flow continues, whereby cavitation is avoided.

4. A gradient former in accordance with claim 3 including:
    a plurality of sources of influents;
    said inlet valve means including a plurality of valves for connecting said gradient pump means to selected ones of said sources of influent; and
    said inlet valve means including means for selectively opening and closing said valves, and in a coordinated manner, controlling the speed of operation of said gradient pump so that, before said valves are opened, said pump speed is slowed, and after said valves are fully opened, said pump speed is increased, whereby cavitation is avoided in supplying liquid to said replaceable pump.

5. A gradient former in accordance with claim 4 in which said valves are electrically-operated automatically-controlled valves.

6. A gradient former in accordance with claim 5 in which said valves are computer controlled.

7. A gradient former according to claim 6 in which said reservoir means is a mixer.

8. A gradient former according to claim 7 in which said inlet valve means includes a valve tree communicating with a plurality of containers for solvents.

9. A gradient former according to claim 8 in which:
    said gradient pump is a low-pressure piston pump having a chamber; and
    said inlet valve means includes means for supplying any of a plurality of different solvents to said gradient pump means as the chamber of said gradient pump means is being filled.

10. A gradient former according to claim 9 in which said valve tree includes two, three-way valves in a binary system, whereby when one path from a solvent source is opened the other is inherently closed.

11. A gradient former according to claim 9 in which said gradient pump has three pumping rates, low medium and high; said low rate being in effect during valve switching, the medium rate being in effect while said valves are fully open, said high rate being in effect during delivery; the ratio of low rate to medium rate varying within a range of ratios of between the ratio of 1 to 1.5 and a ratio of 1 to 5 and the ratio of medium rate to high rate varying within a range of ratios of between the ratio of 1 to 1.5 and the ratio of 1 to 10.

12. A gradient former adapted to supply gradient to a replaceable pump comprising from a plurality of sources of liquid:

gradient pump means having a pump cycle and a refill cycle for pumping liquid;

valve system means for establishing communication between said gradient pump means and selected ones of said sources of liquids;

said valve system means including a plurality of valves;

means for detecting the opening of at least one valve in said plurality of valves and distinguishing between a condition in which the valves are opening and a fully opened condition;

means for storing the time of initiation of opening of said at least one valve and the reaching of the fully opened condition of said at least one valve;

means for storing a program including information concerning the ratio of mixtures of solvents;

means for opening valves between different solvent sources for predetermined periods of time to establish said mixture; and said means for storing the time of valve energization and valve open condition including means for correcting the time of energization to accommodate changes in time required to open valves.

13. A gradient former including:

a plurality of sources of influents and an outlet;

a valve system with a plurality of valves for connecting said outlet to selected ones of said sources of influents;

means for producing a flow of fluid through at least one of said valves;

control means cooperating with said valves to time proportion flow originating from at least two of the sources of influents;

valve energizing means activated by said control means for changing said selection of influent;

valve position detecting means which produces a sensing signal in response to changes in valve position after said valve energizing means is activated; and said control means activating said energizing means at a time at least partly based upon a previous signal from said valve position detecting means.

14. A gradient former according to claim 13 in which the control means advances the time of said activation of a valve energization by an amount directly dependent upon the time elapsed between a previous activation of the same valve and the time of its sensed change in position.

* * * * *